US009884012B2

(12) United States Patent
Tsao et al.

(10) Patent No.: US 9,884,012 B2
(45) Date of Patent: Feb. 6, 2018

(54) USE OF PEDF-DERIVED POLYPEPTIDES FOR PROMOTING MUSCLE OR TENDON REGENERATION OR ARTERIOGENESIS

(75) Inventors: Yeou-Ping Tsao, Taipei (TW); Tsung-Chuan Ho, Taipei (TW)

(73) Assignee: MacKay Memorial Hospital, Taipei (TW)

( * ) Notice: Subject to any disclaimer, the term of this patent is extended or adjusted under 35 U.S.C. 154(b) by 0 days.

(21) Appl. No.: 14/420,581

(22) PCT Filed: Aug. 9, 2012

(86) PCT No.: PCT/CN2012/079897
§ 371 (c)(1),
(2), (4) Date: Feb. 9, 2015

(87) PCT Pub. No.: WO2014/023007
PCT Pub. Date: Feb. 13, 2014

(65) Prior Publication Data
US 2016/0000862 A1  Jan. 7, 2016

(51) Int. Cl.
A61K 38/16 (2006.01)
A61K 38/10 (2006.01)
C07K 14/47 (2006.01)
C07K 14/435 (2006.01)
C07K 7/08 (2006.01)
A61K 9/00 (2006.01)
A61K 47/42 (2017.01)
A61K 38/17 (2006.01)
C07K 14/81 (2006.01)
C07K 14/475 (2006.01)
A61K 38/00 (2006.01)

(52) U.S. Cl.
CPC ............ *A61K 9/0019* (2013.01); *A61K 38/10* (2013.01); *A61K 38/17* (2013.01); *A61K 47/42* (2013.01); *C07K 7/08* (2013.01); *C07K 14/47* (2013.01); *C07K 14/475* (2013.01); *C07K 14/811* (2013.01); *A61K 38/00* (2013.01)

(58) Field of Classification Search
None
See application file for complete search history.

(56) References Cited

U.S. PATENT DOCUMENTS

| 2009/0069241 A1 | 3/2009 | Barnstable et al. |
| 2010/0047212 A1 | 2/2010 | Farinas Gomez et al. |
| 2012/0245097 A1 | 9/2012 | Tsao et al. |

FOREIGN PATENT DOCUMENTS

| CN | 101544696 A | 9/2009 |
| CN | 101977931 A | 2/2011 |
| CN | 102183661 A | 9/2011 |
| CN | 102690344 A | 9/2012 |
| WO | 2004/028559 A1 | 4/2004 |
| WO | 2010-037395 A2 | 4/2010 |

OTHER PUBLICATIONS

Mueller et al., Mol. Cancer Res., 2009, vol. 7(7):1078-1085.*
First Examination Report dated Jun. 5, 2015, issued by the New Zealand Intellectual Property Office in corresponding New Zealand Patent Application No. 705492 (2 pages).
Patent Examination Report No. 1 dated Oct. 15, 2015, by the Australian Patent Office in corresponding Australian Patent Application No. AU-2012387503 (2 pages).
Official Action dated Oct. 22, 2015, issued by the Israel Patent Office in corresponding Israeli Patent Application No. 237137, with partial English translation (6 pages).
Official Action dated Feb. 2, 2016, issued by the Japan Patent Office in related Japanese Patent Application No. JP 2015-525704 (4 pages).
International Search Report issued in PCT/CN2012/079897 dated May 23, 2013 (4 pages).
Examiner's Requisition (Office Action) and Examination Search Report dated Nov. 30, 2015, issued by the Canadian Intellectual Property Office in related Canadian Patent Application No. CA 2,882,479 (4 pages).
Extended European Search Report dated Jan. 5, 2016, issued by the European Patent Office, Munich, Germany, in related European Patent Application No. EP-12882702.9 (5 pages).
Nakamura, Kazuo, et al., "Pigment Epithelium-Derived Factor Inhibits Neointimal Hyperplasia after Vascular Injury by Blocking NADPH Oxidase-Mediated Reactive Oxygen Species Generation"; The American Journal of Pathology, vol. 170, No. 6, Jun. 1, 2007; XP055235956, DOI: 10.2353/ajpath.2007.060838; pp. 2159-2170.
Famulla, S., et al., "Pigment epithelium-derived factor (PEDF) is one of the most abundant proteins secreted by human adipocytes and induces insulin resistance and inflammatory signaling in muscle and fat cells"; International Journal of Obesity, vol. 35, No. 6, Oct. 12, 2010; XP055235996, GB; ISSN: 0307-0565, DOI: 10.1038/ijo. 2010.212; pp. 762-772.
EPO Communication pursuant to Article 94(3) EPC (Office Action) dated Aug. 29, 2016, issued by the European Patent Office in related European Patent Application No. 12882702.9 (5 pages).
Office Action dated Sep. 2, 2016, issued by the Eurasian Patent Office in corresponding Eurasian Patent Application No. 201590329/28, with English translation (3 pages).
Office Action issued in Korean Application No. 10-2015-7005611; dated Sep. 27, 2016 (6 pages).

(Continued)

*Primary Examiner* — Xiaozhen Xie
(74) *Attorney, Agent, or Firm* — Osha Liang LLP

(57) ABSTRACT

A method for promoting muscle or tendon regeneration, and/or arteriogenesis in a subject includes administering to the subject a pharmaceutical composition that contains a synthetic peptide, which has an amino acid sequence that has 20-39 amino acid residues and has at least 20 consecutive residues that has at least 90% amino acid sequence identity to residues 11-30 of SEQ ID NO: 1. The synthetic peptide may have the amino acid sequence of SEQ ID NO: 1, SEQ ID NO: 2, SEQ ID NO: 3, SEQ ID NO: 5, SEQ ID NO: 6, SEQ ID NO: 8, or SEQ ID NO: 9.

20 Claims, 10 Drawing Sheets

(56) References Cited

OTHER PUBLICATIONS

First Office Action dated Jan. 4, 2016, by The State Intellectual Property Office (SIPO) of The Peoples Republic of China in related Chinese Application No. CN-201280075699.7 (8 pages), with English translation (5 pages).
EPO Communication pursuant to Article 94(3) EPC (Office Action) dated Mar. 14, 2017, issued by the European Patent Office in corresponding European Application No. 12882702.9 (5 pages).
Notification of Grounds for Refusal (Office Action) dated Mar. 15, 2017, by the Korean Intellectual Property Office (KIPO) in corresponding Korean Patent Application No. KR 10-2015-7005611, with English translation (12 pages).
Final Office Action dated Dec. 20, 2016, issued by the Japan Patent Office in related Japanese Patent Application No. JP 2015-525704, with Google machine English translation (15 pages).
Second Examiner's Requisition (Office Action) dated Dec. 12, 2016, by the Canadian Intellectual Property Office (CIPO) in related Canadian Patent Application No. CA-2882479 (5 pages).
Office Action issued in Eurasian Application No. 201590329/28; dated May 5, 2017, with English translation (4 pages).
Office Action issued in Chinese Application No. 201280075699.7; dated Sep. 13, 2017 (10 pages).

* cited by examiner

USE OF PEDF-DERIVED POLYPEPTIDES FOR PROMOTING MUSCLE OR TENDON REGENERATION OR ARTERIOGENESIS

CROSS REFERENCE TO RELATED APPLICTIONS

This is a national phase application based on PCT/CN2012/079897, filed on Aug. 9, 2012, the disclosure of which is incorporated by reference in its entirety.

BACKGROUND OF THE INVENTION

1. Field of the Invention

The present disclosure relates to the treatment of tissue damages. In particular, the disclosed invention relates to the use of PEDF-derived polypeptides for promoting muscle or tendon regeneration or arteriogenesis in the treatment of tissue damages.

2. Description of Related Art

Muscle tissues are classified as skeletal, cardiac or smooth muscles. Muscle is capable of repairing its damage. After injury, skeletal muscle is repaired by a spontaneous process to remove damaged myofibers and synthesizing new muscle fibers. However, such spontaneous tissue repair mechanism is absent in some tissue damage or inadequate to effect a full recovery of the tissue. For example, some pathologic conditions (such as severe injury, advanced age, muscle disuse, cancer, and tissue ischemia) or genetic defects (such as muscular dystrophy) may lead to impaired healing. Failure of repair may lead to permanent loss of muscle mass, disease progression, and functional deficiency.

A tendon is a tough band of fibrous connective tissue that usually connects muscle to bone. Tendon injuries generally result in inflammation and degeneration or weakening of the tendons, which may eventually lead to tendon rupture. Tendon healing is a long and intricate process that typically takes months, and over a time period of about one year, the tissue will gradually turn from fibrous to scar-like. Such scar tissue may result in reduced elasticity and mobility of the tendon and increased propensity for recurrence of injury. Tendon-derived stem cells (TSCs) and bone marrow-derived mesenchymal stem cells (BM-MSCs) offer limited autologous healing of tendonitis lesions.

Episodes of ischemia are another cause of considerable tissue damage. Ischemic episodes leading to tissue damage result in myocardial infarctions, stroke, and other disorders. Short episodes of ischemia cause mild damage from which a cell can recover, while longer periods of ischemia cause irreversible cell damage, leading to cell death. In the latter case, even if blood circulation is reestablished, total functional recovery of the damaged cell is impossible. Furthermore, loss of function always precedes cell death.

No present treatment for these conditions offers a cure or facilitates regeneration of the damaged, nonfunctional tissue. Thus, there exists a need in the art for means that promotes regeneration of tissue. In particular, it would be desirable to provide a composition and method for promoting arteriogenesis so as to promote blood flow in or adjacent to the damaged tissue region and to permit quasi-normal function to the tissue.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

The present disclosure is based, at least, on the finding that synthetic peptides derived from pigment epithelium-derived factor (PEDF) may promote the muscle regeneration or tendon regeneration as well as arteriogenesis in a subject. The PEDF-derived synthetic peptides of this invention are, therefore, useful as an agent or a medicament for treating tissue damages (in particular, those associated with ischemia).

Accordingly, in one aspect, the present disclosure is directed to a synthetic peptide for promoting muscle or tendon regeneration in a subject.

According to embodiments of the present disclosure, the synthetic peptide is 20-39 amino acid residues in length, and has an amino acid sequence that is at least 80% identical to SEQ ID NO: 1. Also, the amino acid sequence comprises at least 20 consecutive residues, which is at least 90% identical to residues 11-30 of SEQ ID NO: 1, such that the synthetic peptide is useful in promoting the muscle or tendon regeneration in a subject.

According to optional embodiments of the present disclosure, at least 4 consecutive residues of the synthetic peptide are identical to residues 11-14 of SEQ ID NO: 1. Non-limiting examples of such synthetic peptides include those respectively having an amino acid sequence of SEQ ID NO: 1 (39-mer), SEQ ID NO: 2 (34-mer), SEQ ID NO: 3 (29-mer), SEQ ID NO: 5 (24-mer), SEQ ID NO: 6 (20-mer), SEQ ID NO: 8 (MO 29-mer), and SEQ ID NO: 9 (MO 20-mer). In some embodiments of the present disclosure, the amino acid sequence of the synthetic peptide is any of SEQ ID NO: 3 (29-mer), SEQ ID NO: 5 (24-mer), or SEQ ID NO: 6 (20-mer).

In another aspect, the present disclosure is directed to a pharmaceutical composition for promoting muscle or tendon regeneration in a subject. The subject may be any animal classified as a mammal, including human.

According to one embodiment of the present disclosure, the pharmaceutical composition comprises a synthetic peptide according to any of the above-mentioned aspect/embodiments, and the synthetic peptide is present in an effective amount sufficient to promote muscle or tendon regeneration in the subject. The pharmaceutical composition also comprises a pharmaceutically acceptable carrier for the synthetic peptide.

According to optional embodiments of the present disclosure, the pharmaceutically acceptable carrier is a polymeric material, which may be any of alginate, gelatin, collagen, or poly(lactide-co-glycolide).

According to optional embodiments of the present disclosure, the synthetic peptide is present in the pharmaceutical composition in an amount of about 1-100 μM, and preferably, about 10 μM.

In yet another aspect, the present invention is directed to a method for promoting muscle or tendon regeneration in or adjacent to a damaged region of a subject. The subject may be any animal classified as a mammal, including human.

In one embodiment, the method comprises administering, to a treatment region of the subject, a therapeutically effective amount of the synthetic peptide according to the above-mentioned aspect/embodiments of the present disclosure, wherein the treatment region is adjacent to the damaged region so as to promote muscle or tendon regeneration in or adjacent to the damaged region of the subject.

According to optional embodiments, the synthetic peptide is formulated into a pharmaceutical composition according to the above-mentioned aspect/embodiments of the present disclosure. In practice, the pharmaceutical composition may be administered via intramuscular injection.

According to some embodiments, the subject may be suffering from muscle injury, muscle disuse, muscular dystrophy, amyotrophic lateral sclerosis, tendon injury, tissue ischemia, cerebral ischemia, peripheral arterial diseases, or myocardial infarction, which causes the muscle or tendon damage in the damaged region.

Also, in another aspect, the present disclosure is directed to a synthetic peptide for promoting arteriogenesis in a subject. The subject may be any animal classified as a mammal, including human.

According to embodiments of the present disclosure, the synthetic peptide is 20-39 amino acid residues in length, and has an amino acid sequence that is at least 80% identical to SEQ ID NO: 1. Also, the amino acid sequence comprises at least 20 consecutive residues, which is at least 90% identical to residues 11-30 of SEQ ID NO: 1, such that the synthetic peptide is useful in promoting the arteriogenesis in a subject.

According to optional embodiments of the present disclosure, at least 4 consecutive residues of the synthetic peptide are identical to residues 11-14 of SEQ ID NO: 1. Non-limiting examples of such synthetic peptides include those respectively having an amino acid sequence of SEQ ID NO: 1 (39-mer), SEQ ID NO: 2 (34-mer), SEQ ID NO: 3 (29-mer), SEQ ID NO: 5 (24-mer), SEQ ID NO: 6 (20-mer), SEQ ID NO: 8 (MO 29-mer), and SEQ ID NO: 9 (MO 20-mer). In some embodiments of the present disclosure, the amino acid sequence of the synthetic peptide is any of SEQ ID NO: 3 (29-mer), SEQ ID NO: 5 (24-mer), or SEQ ID NO: 6 (20-mer).

In another aspect, the present disclosure is directed to a pharmaceutical composition for promoting arteriogenesis in a subject. The subject may be any animal classified as a mammal, including human.

According to one embodiment of the present disclosure, the pharmaceutical composition comprises a synthetic peptide according to any of the above-mentioned aspect/embodiments, and the synthetic peptide is present in an effective amount sufficient to promote arteriogenesis in the subject. The pharmaceutical composition also comprises a pharmaceutically acceptable carrier for the synthetic peptide.

According to optional embodiments of the present disclosure, the pharmaceutically acceptable carrier is a polymeric material, which may be any of alginate, gelatin, collagen, or poly(lactide-co-glycolide).

According to optional embodiments of the present disclosure, the synthetic peptide is present in the pharmaceutical composition in an amount of about 1-100 µM, and preferably, about 10 µM.

In yet another aspect, the present invention is directed to a method for promoting arteriogenesis in or adjacent to an ischemic region of a subject. The subject may be any animal classified as a mammal, including human.

In one embodiment, the method comprises administering, to a treatment region of the subject, a therapeutically effective amount of the synthetic peptide according to the above-mentioned aspect/embodiments of the present disclosure, wherein the treatment region is adjacent to the ischemic region so as to promote arteriogenesis in or adjacent to the ischemic region of the subject.

According to optional embodiments, the synthetic peptide is formulated into a pharmaceutical composition according to the above-mentioned aspect/embodiments of the present disclosure. In practice, the pharmaceutical composition may be administered via intramuscular injection.

According to some embodiments, the subject may be suffered from muscle injury, muscle disuse, muscular dystrophy, amyotrophic lateral sclerosis, tendon injury, tissue ischemia, cerebral ischemia, peripheral arterial diseases, or myocardial infarction, which causes the blood flow at the ischemic region to be hindered or blocked.

Many of the attendant features and advantages of the present disclosure will becomes better understood with reference to the following detailed description considered in connection with the accompanying drawings.

BRIEF DESCRIPTION OF THE DRAWINGS

The present description will be better understood from the following detailed description read in light of the accompanying drawings.

DESCRIPTION

Figure 1:
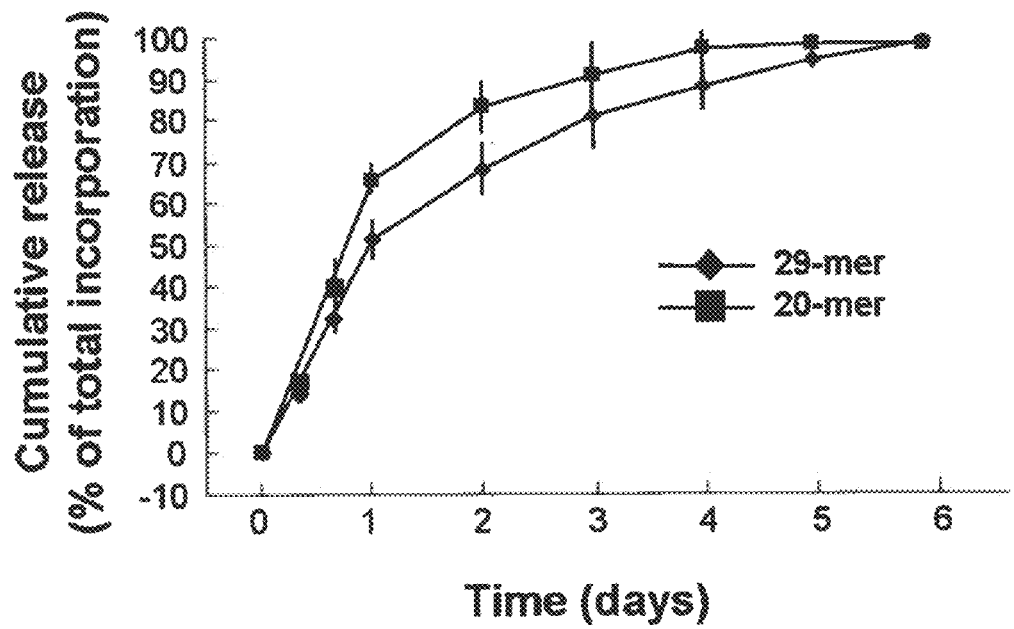
FIG. 1 illustrates the cumulative in vitro release of PEDF peptides from alginate gel in PBS at 37° C. The results are presented as the means±standard deviation for three separate experiments.

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

For convenience, certain terms employed in the entire application (including the specification, examples, and appended claims) are collected here. Unless otherwise defined herein, scientific and technical terminologies employed in the present disclosure shall have the meanings that are commonly understood and used by one of ordinary skill in the related art. Unless otherwise required by context, it will be understood that singular terms shall include plural forms of the same and plural terms shall include the singular. Specifically, as used herein and in the claims, the singular forms "a" and "an" include the plural reference unless the context clearly indicates otherwise.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

As used herein, the term "peptide" denotes a polymer of amino acid residues. By the term "synthetic peptide" as used herein, it is meant a peptide which does not comprise an entire naturally occurring protein molecule. The peptide is "synthetic" in that it may be produced by human intervention using such techniques as chemical synthesis, recombinant genetic techniques, or fragmentation of the whole protein or the like. Throughout the present disclosure, the positions of any specified amino acid residues within a peptide are numbered starting from the N terminus of the peptide.

The term "stem cell" as used herein, refers to a cell that retains the capacity, under certain circumstances, to proliferate without substantially differentiating; as well as the capacity or potential, under particular circumstances, to differentiate to a more specialized or differentiated phenotype.

As used herein, "proliferating" and "proliferation" refers to an increase in the number of cells in a population by means of cell division.

As used herein, the term "muscle cell" refers to any cell which contributes to muscle tissue, and encompasses myoblasts, satellite cells, myotubes, and myofibril tissues. "Muscle regeneration" as used herein refers to the process by which new muscle fibers form from muscle progenitor cells. The regeneration of muscle in or adjacent to the damaged region may be evidenced by the increase in the number, diameter (size), wet weight, and/or the protein content of the muscle fibers in or adjacent to the damaged region. Also, the muscle regeneration may be monitored by the proliferative activity of muscle cells and/or satellite cells in or adjacent to the damaged region.

As used herein, the term "tendon" refers to a fibrous tissue composed of parallel arrays of closely packed collagen fibers that connects muscle to bone. The healing of damaged tendon is a slow process and usually associated with scar formation which may result in a defective tendon that cannot resume normal or original tendon function. As used herein, the term "tendon regeneration" refers to a tendon healing process in which type I collagen is formed, and the newly formed collagen fibers align parallel to the direction of load application, whereby resulting in minimal scar formation. The regeneration of tendon in or adjacent to the damaged region may be evidenced by the increase in the number of the collagen fibrils with an organized orientation in or adjacent to the damaged region. Also, the tendon regeneration may be monitored by the proliferative activity of tendon stem cells in or adjacent to the damaged region.

As used herein, the term "arteriogenesis" is to be distinguished from "angiogenesis." Angiogenesis is a process by which new capillary blood vessels sprout from a pre-existing blood vessel. It is important to recognize that these newly formed capillary tubes lack vascular smooth muscle cells. Accordingly, they are fragile and prone to rupture. These capillary tubes would not go through vasculature remodeling process, and hence are unable to sustain and/or restore proper circulation in and/or adjacent to the damaged region. In contrast to the capillary sprouting, arteriogenesis refers to the in situ recruitment and expansion of arteries or collateral arteries by proliferation of endothelial and smooth muscle cells from pre-existing arteriolar connections. These newly formed arteries or collateral arteries would develop into a functional network of arteries (or collateral arteries) which constitute natural bypasses capable of supplying sufficient blood to the damaged or ischemic tissue or site of inflammation.

The term "ischemia" as used herein relates to a condition that may occur in any tissue and/or organ that suffers from a lack of oxygen supply and/or from abnormal accumulation of metabolites, which occurs when there is an imbalance between oxygen supply and demand, due to inadequate perfusion, e.g., caused by atherosclerosis, restenotic lesions, anemia, stroke or clogged arteries just to name a few, that leads to insufficient oxygen to tissues such as, for example, the muscle, heart or brain. However, ischemia is not limited to the aforementioned organs or tissues, since it may occur in any organ/tissue.

The term "promote" or "promoting" is meant to refer to a positive alteration; in particular a statistically significant positive alteration. The positive alteration means an increase of at least 10% as compared to a reference level.

"Percentage (%) amino acid sequence identity" with respect to the synthetic polypeptide sequences identified herein is defined as the percentage of amino acid residues in a candidate sequence that are identical with the amino acid residues in the specific polypeptide sequence, after aligning the sequences and introducing gaps, if necessary, to achieve the maximum percent sequence identity, and not considering any conservative substitutions as part of the sequence identity. Alignment for purposes of determining percentage sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, sequence comparison between two amino acid sequences was carried out by computer program Blastp (protein-protein BLAST) provided online by Nation Center for Biotechnology Information (NCBI). The percentage amino acid sequence identity of a given amino acid sequence A to a given amino acid sequence B (which can alternatively be phrased as a given amino acid sequence A that has a certain % amino acid sequence identity to a given amino acid sequence B) is calculated by the formula as follows:

$$\frac{X}{Y} \times 100\%$$

where X is the number of amino acid residues scored as identical matches by the sequence alignment program BLAST in that program's alignment of A and B, and where Y is the total number of amino acid residues in A or B, whichever is shorter.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject agents from one organ, or a portion of the body, to another organ, or another portion of the body. Each carrier must be "acceptable" in the sense of being compatible with the other ingredients of the formulation. The carrier can be in the form of a solid, semi-solid, or liquid diluent, cream or a capsule.

The terms "treatment" and "treating" are used herein to generally mean obtaining a desired pharmaceutical and/or physiological effect. Preferably, the effect is therapeutic in terms of partially or completely curing the muscle damage, tendon damage, or ischemia. The term "treating" as used herein refers to application or administration of the synthetic peptide or pharmaceutical composition of the present disclosure to a subject, who has a medical condition, a symptom of the condition, a disease or disorder secondary to the condition, or a predisposition toward the condition, with the purpose to partially or completely alleviate, ameliorate, relieve, delay onset of, inhibit progression of, reduce severity of, and/or reduce incidence of one or more symptoms or features of a particular disease, disorder, and/or condition. Treatment may be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition. Treatment is generally "effective" if one or more symptoms or clinical markers are reduced as that term is defined herein. Alternatively, a treatment is "effective" if the progression of a disease is reduced or halted. That is, "treatment" includes not just the improvement of symptoms or decrease of markers of the disease, but also a cessation or slowing of progress or worsening of a symptom that would be expected in absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, and remission (whether partial or total), whether detectable or undetectable.

The term "effective amount" as used herein refers to the quantity of a component which is sufficient to yield a desired response. The term "therapeutically effective amount" as used herein refers to the amount of therapeutically agent of pharmaceutical composition to result in a desired "effective treatment" as defined hereinabove. The specific therapeutically effective amount will vary with such factors as the particular condition being treated, the physical condition of the patient (e.g., the patient's body mass, age, or gender), the type of mammal or animal being treated, the duration of the treatment, the nature of concurrent therapy (if any), and the specific formulations employed. A therapeutically effective amount is also one in which any toxic or detrimental effects of the compound or composition are outweighed by the therapeutically beneficial effects.

The term "subject" refers to a mammal including the human species that is treatable with the synthetic peptides, compositions, and/or methods of the present invention. The term "subject" is intended to refer to both the male and female gender unless one gender is specifically indicated.

Pigment epithelium-derived factor (PEDF) is a multifunctional secreted protein that has anti-angiogenic, anti-tumorigenic, and neurotrophic functions. Human PEDF protein (SEQ ID No: 14) is a secreted protein of roughly 50 kDa size and 418 amino acids in length. A 34-mer fragment (residues 44-77) and a 44-mer fragment (residues 78-121) of PEDF have been identified to have anti-angiogenic and neurotrophic properties, respectively.

The present disclosure is based, at least, on the finding that synthetic peptides derived from PEDF may promote the regeneration of muscle or tendon tissue and arteriogenesis in a subject. In particular, the present disclosure is the first to identify a link between the local delivery of PEDF-derived peptides and the healing of muscle or tendon tissues suffering from damage and/or ischemia or the formation of (collateral) arteries in or adjacent to the ischemic region. Another inventive feature of the present invention lies in that the synthetic peptides are much shorter (39 amino acid residues at most) than the full-length PEDF and thus overcomes the limitations associated with the clinical use of conventional protein drugs, including high manufacturing cost, low bioavailability, and poor pharmacokinetics. Accordingly, the present synthetic peptides are useful for treating muscle or tendon damages as well as tissues or organs suffering from ischemia.

Thus, in one aspect, the present disclosure is directed to a synthetic peptide for promoting muscle or tendon regeneration in a subject. In another aspect, the present disclosure is directed to a synthetic peptide for promoting arteriogenesis in a subject. Embodiments applicable to either or both of these two aspects are discussed below.

According to embodiments of the present disclosure, the synthetic peptide has 20-39 amino acid residues in length, and has at least 80% amino acid sequence identity with the amino acid sequence of LSVATALSALSLGAEQRTESIIHRALYYDLISSPDIHGT (SEQ ID NO: 1). For example, the synthetic peptide may have an amino acid sequence identity of about 80, 81, 82, 83, 84, 85, 86, 87, 88, 89, 90, 91, 92, 93, 94, 95, 96, 97, 98, 99, or 100 percent with SEQ ID NO: 1. Also, the synthetic peptide comprises at least 20 consecutive residues that are at least 90% identical to residues 11-30 of SEQ ID NO: 1. Specifically, the 20 consecutive amino acid residues may have about 90, 91, 92, 93, 94, 95, 96, 97, 98, 99, or 100 percent amino acid sequence identity with residues 11-30 of SEQ ID NO: 1.

In one embodiment, the synthetic peptide has the sequence of SEQ ID NO: 1, which has 39 amino acids in length. This synthetic peptide is referred to as 39-mer in the description hereinbelow. This 39-mer peptide corresponds to residues 83-121 of human PEDF and hence is a short variant derived from the known PEDF 44-mer (corresponding to residues 78-121 of PEDF).

Prior experiments conducted by the present inventors, such as those disclosed in the co-pending application U.S. Ser. No. 13/428,996, the entirety of which is incorporated herein by reference, and experiments provided hereinbelow, reveal that several short, synthetic PEDF peptides derived from the 39-mer, are capable of promoting muscle or tendon regeneration and/or arteriogenesis in a subject.

For example, based on experiments disclosed in both the prior application and the present application, a 34-mer synthetic peptide having the sequence of ALSALSLGAEQRTESIIHRALYYDLISSPDIHGT (SEQ ID NO: 2) is effective in promoting muscle or tendon regeneration and/or arteriogenesis in a subject. This 34-mer peptide corresponds to residues 88-121 of human PEDF. According to the process for estimating percentage of sequence identity between any two given sequences provided above, the 34-mer has a 100% amino acid sequence identity to the 39-mer, and the $6^{th}$-$25^{th}$ amino acid residues of the 34-mer has a 100% amino acid sequence identity to the amino acid residues 11-30 of the 39-mer.

Additionally, according to various examples hereinbelow, a 29-mer synthetic peptide having the sequence of SLGAEQRTESIIHRALYYDLISSPDIHGT (SEQ ID NO: 3) has been confirmed to be effective in promoting muscle or tendon regeneration as well as arteriogenesis in a subject. This 29-mer peptide corresponds to residues 93-121 of human PEDF with a 100% amino acid sequence identity to the 39-mer. Also, the $1^{st}$-$20^{th}$ amino acid residues of the 29-mer has a 100% amino acid sequence identity to the amino acid residues 11-30 of the 39-mer.

In some examples, a 24-mer has been confirmed to be effective in promoting tendon regeneration and arteriogenesis in a subject. The 24-mer has the sequence of SLGAEQRTESIIHRALYYDLISSP (SEQ ID NO: 5), which corresponds to residues 93-116 of human PEDF. This 24-mer peptide has a 100% amino acid sequence identity to the 39-mer in which the first twenty amino acid residues thereof has a 100% amino acid sequence identity to the amino acid residues 11-30 of the 39-mer.

In other examples, it has been established that a 20-mer may promote muscle or tendon regeneration as well as arteriogenesis in a subject. The 20-mer has the sequence of SLGAEQRTESIIHRALYYDL (SEQ ID NO: 6), which corresponds to residues 93-112 of human PEDF. This 20-mer peptide is completely identical to the amino acid residues 11-30 of the 39-mer (100% amino acid sequence identity), and has a 100% amino acid sequence identity to the 39-mer.

Two synthetic peptides derived from mouse PEDF may also promote muscle or tendon regeneration and/or arteriogenesis in a subject based on experiments disclosed in both the prior application and the present application. The first mouse-derived peptide is referred to as "Mo 29-mer" in the present disclosure. The Mo 29-mer has a sequence of SLGAEHRTESVIHRALYYDLITNPDIHST (SEQ ID NO: 8), which has a 83% amino acid sequence identity to 39-mer, and the first 20 amino acid residues thereof has a 90% amino acid sequence identity to the 11-30 amino acid residues of the 39-mer. Another mouse-derived peptide, Mo 20-mer has a sequence of SLGAEHRTESVIHRALYYDL (SEQ ID NO: 9). The Mo 20-mer has a 90% amino acid sequence identity to either the 39-mer or the 11-30 amino acid residues of the 39-mer.

Optionally, the synthetic peptide comprises 4 consecutive residues identical to residues 11-14 of SEQ ID NO: 1. It is believed that residues 11-14 (i.e., SLGA) of SEQ ID NO: 1 play an important role in maintaining the biological function of the short PEDF peptides. For example, according to various examples provided below, a 18-mer peptide (EQRTESIIHRALYYDLIS; SEQ ID NO: 7) without the SLGA residues fail to elicit any arteriogenesis in a subject. Also, based on experiments disclosed in both the prior application and the present application, it is suggested that a 25-mer peptide (EQRTESIIHRALYYDLISSPDIHGT; SEQ ID NO: 4) is ineffective in promoting muscle or tendon regeneration and/or arteriogenesis in a subject.

The synthetic Peptides of the invention can be synthesized by commonly used methods such as t-BOC or FMOC protection of alpha-amino groups. Both methods involve stepwise syntheses whereby a single amino acid is added at each step starting from the C terminus of the peptide. Peptides of the present invention can also be synthesized by the well-known solid phase peptide synthesis methods.

Other synthetic peptides with conservative variation with respect to the 39-mer are also contemplated. The term "conservative variation" as used herein denotes the replacement of an amino acid residue by another, biologically similar residue. Examples of conservative variations include the substitution of one hydrophobic residue such as isoleucine, valine, leucine or methionine for one another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

The synthetic peptides according to above-mentioned embodiments may be formulated into pharmaceutical compositions for promoting muscle or tendon regeneration and/or arteriogenesis in a subject, which falls within other aspects of the present disclosure.

According to one embodiment of the present disclosure, the pharmaceutically composition comprises a synthetic peptide according to any of the above-mentioned aspects/embodiments, and the synthetic peptide is present in an effective amount sufficient to promote the muscle or tendon regeneration and/or arteriogenesis in the subject. The pharmaceutical composition also comprises a pharmaceutically acceptable carrier for the synthetic peptide.

The choice of a pharmaceutically acceptable carrier to be used in conjunction with a synthetic peptide is basically determined by the way the pharmaceutical composition is to be administered. According to one optional embodiment of the present disclosure, the pharmaceutical composition may be administered locally via intramuscular injection. In this case, the synthetic peptide may be formulated with a pharmaceutically acceptable carrier such as a sterile aqueous solution, which is preferably isotonic with the blood of the recipient. Such formulations may be prepared by dissolving or suspending the solid active ingredient in water containing physiologically compatible substances such as sodium chloride, glycine, and the like, and having a buffered pH compatible with physiological conditions to produce an aqueous solution, and rendering said solution sterile.

Still optionally, the synthetic peptide may be formulated in a sustained-release dosage form so as to ensure a more prolonged therapeutic action of the treatment. There are several polymeric materials suitable for prolonging drug release, examples of which include, but are not limited to, alginate, gelatin, collagen, and poly(lactide-co-glycolide).

According to some working examples of the present disclosure, the present synthetic peptides are embedded in a matrix of cross-linked alginate gel, and the final concentration of the synthetic peptides is about 1-100 µM, and preferably, about 10 µM. For example, the concentration of the synthetic peptides may be about 1, 2, 3, 4, 5, 6, 7, 8, 9, 10, 15, 20, 25, 30, 35, 40, 45, 50, 55, 60, 65, 70, 75, 80, 85, 90, 95, or 100 µM.

Pharmaceutical compositions of the invention can also comprise various additives known to those skilled in the art. For example, solvents, including relatively small amounts of alcohol, may be used to solubilize certain drug substances. Other optional pharmaceutically acceptable additives include opacifiers, antioxidants, fragrance, colorant, gelling agents, thickening agents, stabilizers, surfactants, and the like. Other agents may also be added, such as antimicrobial agents, to prevent spoilage upon storage, i.e., to inhibit growth of microbes such as yeasts and molds. Permeation enhancers and/or irritation-mitigating additives may also be included in the composition of the present invention.

In yet another aspect, the present invention is directed to a method for promoting muscle or tendon regeneration in or adjacent to a damaged region of a subject; and in still another aspect, the present invention is directed to a method for promoting arteriogenesis in or adjacent to an ischemic region of a subject. In either embodiment, the subject may be any animal classified as a mammal, including human. Embodiments applicable to either or both of these two aspects are discussed below.

In one embodiment, the method for promoting muscle or tendon regeneration in or adjacent to a damaged region of a subject comprises administering, to a treatment region of the subject, a therapeutically effective amount of the synthetic peptide of the present disclosure, wherein the treatment region is adjacent to the damaged region so as to promote the muscle or tendon to regenerate in or adjacent to the damaged region of the subject to regenerate.

In another embodiment, the method for promoting arteriogenesis in or adjacent to an ischemic region of a subject comprises administering, to a treatment region of the subject, a therapeutically effective amount of the synthetic peptide of the present disclosure, wherein the treatment region is adjacent to the ischemic region, so as to promote arteriogenesis in or adjacent to the ischemic region of the subject.

According to optional embodiments, the synthetic peptide is formulated in a pharmaceutical composition according to the above-mentioned aspect/embodiments of the present disclosure. In practice, the pharmaceutical composition may be administered via intramuscular injection.

According to some embodiments, the subject may be suffering from muscle injury, muscle disuse, muscular dystrophy, amyotrophic lateral sclerosis, tendon injury, tissue ischemia, cerebral ischemia, peripheral arterial diseases, or myocardial infarction, which causes the blood flow at the ischemic region to be hindered or blocked.

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent. All publications cited herein are hereby incorporated by reference in their entirety.

EXAMPLES

Materials and Methods
Materials

Dulbecco's modified Eagle's medium (DMEM), fetal bovine serum (FBS), 0.25% trypsin, anti-BrdU antibody, MCDB131 medium, TRIzol, and Dynabeads were purchased from Invitrogen (Carlsbad, Calif.). Ultrapure alginate (6000 Da), dimethyl sulfoxide (DMSO), bovine serum albumin (BSA), 5-bromo-2'-deoxyuridine (BrdU), Hoechst 33258 dye, and Masson's Trichrome were all from Sigma-Aldrich (St. Louis, Mo.). Collagenase type I and dispase II were obtained from Roche (Indianapolis, Ind.). All the fluorescent dye-conjugated secondary antibodies were purchased from BioLegend (San Diego, Calif.). Hematoxylin and eosin (H&E) dyes were purchased from Merck (Rayway, N.J., USA). Anti-collagen 1A1 antibody was obtained from Santa Cruz Biotechnology (Santa Cruz, Calif.). Matrigel was purchased from BD Biosciences (Bedford, Mass.). Anti-alpha-smooth muscle actin (anti-α-SMA) antibody (ab5694) and anti-nucleostemin antibody were from Abcam (Cambridge, Mass.). Anti-Pax7 antibody (GTX62311) was from GeneTex (Taipei, Taiwan). Isolectin B4 (IB4)-Alexa Fluor 568 was from Molecular Probes (Eugene, Oreg.).

Short synthetic PEDF peptides, including 29-mer (SEQ ID No: 3), 25-mer (SEQ ID No: 4), 24-mer (SEQ ID No: 5), 20-mer (SEQ ID No: 6), 18-mer (SEQ ID No: 7), MO 29-mer (SEQ ID No: 8), and MO 20-mer (SEQ ID No: 9) were synthesized and modified with acetylated at the $NH_2$ termini and amidated at the COOH termini for stability and characterized by mass spectrometry (>95% purity) to order at GenScript (Piscataway, N.J.).

All animals used in embodiments of the present disclosure were housed in an animal room under temperature control (24-25° C.) and 12:12 light-dark cycle. Standard laboratory chow and tap water were available ad libitum. The experiments procedures were approved by the Mackay Memorial Hospital Review Board (New Taipei City, Taiwan, R.O.C.) and were performed in compliance with national animal welfare regulations.

PEDF Peptide/Alginate Gel Formulation and Bolus Formulation

Each PEDF-derived short synthetic peptide (the 29-mer, 25-mer, 24-mer, 20-mer, 18-mer, MO 29-mer, or MO 20-mer; hereinbelow, PEDF peptide) was reconstituted in DMSO as stock (5 mM). Then, ultrapure alginate was mixed with the stock to obtain a 2% wt/vol alginate solution with PEDF peptide at a final concentration of 10 µM. The alginate solution was then filtered by membrane filter (pore size, 0.22 µm) and mixed with filtered calcium sulfate (0.21 g $CaSO_4$/mL of dH2O) at a ratio of 25:1 (40 µL of $CaSO_4$ per 1 mL of the filtered alginate solution). The mixture was let standing at RT for about 1 hour to allow for the cross-linking of the alginate. The resultant sustained-release formulation was then used in the treatment of muscle or tendon damage and ischemia.

For bolus delivery, a final PEDF concentration of 10 µM was used by performing serial dilutions from the 5 mM stock solution.

Histology, Immunohistochemistry and Quantification

The gracilis, adductor magnus, soleus, and tibialis muscles were fixed in 4% paraformaldehyde, dehydrated with graded ethanol series, and paraffinized. Fixed samples were de-paraffinized in xylene and rehydrated in a graded series of ethanol. Tissues were sliced into 5-µm sections. General histology was performed using H&E dye.

De-paraffinized tissue sections were blocked with 10% goat serum for 1 hour. Staining was done using primary antibodies against BrdU (1:50 dilution; GTX42641) or type I collagen 1A1 (1:50 dilution) overnight at 4° C., followed by incubation with the appropriate peroxidase-labeled donkey immunoglobulin for 30 min and then with chromogen substrate (3,3'-diaminobenzidine) for 2 min before counterstaining with hematoxylin. Quantification was estimated based on high quality images (1208×960 pixels) captured using a Nikon Eclipse 80i light microscope.

The muscle fiber size was determined on H&E-stained muscle cross section and quantified using the minimum distance of parallel tangents at opposing particle borders (minimal "Feret's diameter"). Pictures were captured using a Nikon Eclipse 80i light microscope, and the minimal Feret's diameter was measured using the Image-Pro Plus 4.5.1 software (Media Cybernetics). Normalization of the number of fibers in each fiber Feret class of 5 µm was based on the total number of muscle fibers in each picture.

To ascertain the number of centrally nucleated muscle fibers, sections were stained with H&E and then photographed as described above. At least 100 stained fibers were randomly chosen from each photo. Muscle fibers were judged centrally nucleated if one or more nuclei were not located at the periphery of the fiber. The data were expressed as a % of the total number of muscle fibers counted. Results were evaluated from 6 sections per muscle section, and 10 mice at each group.

De-paraffinized tendon tissue sections were stained using Masson's Trichrome according to the manufacturer's instructions. For semi-quantitative analysis of collagen area, 10 fields from each slide were randomly selected under a light microscope, and the repairing area per intact tendon area of the cross section ($mm^2/mm^2$) was measured using the Image-Pro Plus 4.5.1 system.

Isolation and Culture of Tendon Stem Cells

New Zealand White rabbits (6-8 months old, 3.0-4.0 kg) were used in this study. Achilles tendons were removed from the rabbits by cutting through their bony attachments. The tendon sheath was stripped away and the core portion of the tendons was minced into small fragments. Each 100 mg of fragment was then digested in a solution containing 3 mg/mL of type I collagenase and 4 mg/mL of dispase in 1 ml Dulbecco's Modified Eagle Medium (DMEM-high glucose) at 37° C. for 2 hours. The resultant cell suspension was centrifuged at 1,000 rpm for 15 minutes to obtain a cell pellet which was then resuspended in a growth medium consisting of DMEM supplemented with 10% heat inactivated fetal bovine serum (FBS), 100 µM 2-mercaptoethanol, and 100 U/ml penicillin and 100 µg/ml streptomycin. For passage, near-confluent cells were harvested with 0.25% trypsin and then $1 \times 10^5$ subcultured cells were further cultured in medium.

TSCs Proliferation Assay

The TSCs at passage 4 were seeded at gelatin-coated slide in a 6-well plate at a density of $2 \times 10^5$ cells per well and cultured in growth medium (DMEM+10% FBS) for 24 hours before being replaced by a basal growth medium with 5% FBS only (control group) or with 5% FBS plus an additional 50 nM of PEDF-derived peptide (i.e., 29-mer, 24-mer, 20-mer, 18-mer, Mo 29-mer, or Mo 20-mer) for 24 hours. For BrdU labeling assay, BrdU (final concentration, 10 µM) was added to the culture for 4 hours. After fixing with 4% paraformaldehyde, cells were exposed to cold methanol for 2 minutes, and then treated with 1 N HCl at RT for 1 hour before performing immunofluorescence. The phenotype of passage 4 TSC was determined by immunocytochemistry of nucleostemin and type I collagen. Almost all of expanded TSCs were nucleostemin and type I collagen-double positive cells.

In Vivo Detection of DNA Synthesis

For the detection of cell expansion, BrdU was reconstituted in DMSO as stock (80 mM). 10 µl of BrdU mixed with 90 µl of PBS was intraperitoneally injected into the mouse 16 hours prior to euthanasia. Also, 150 µl of BrdU mixed with 350 µl of PBS was intraperitoneally injected into the rat 16 hours prior to euthanasia. DNA synthesis was assessed by BrdU labeling with anti-BrdU antibodies.

Immunofluorescence Analysis

De-paraffinized tissue sections or 4% paraformaldehyde fixed rabbit tendon stem cells (TSCs) were blocked with 10% goat serum and 5% BSA for 1 hour. Double staining was done using primary antibodies against α-SMA (1:100 dilution), IB4 (5 µg/ml), Pax7 (1:100 dilution), nucleostemin (1:100 dilution) and type I collagen 1A1 (1:50) at 37° C. for 2 hours, followed by incubation with the appropriate rhodamine- or FITC-conjugated donkey IgG for 1 hour at RT. Nuclei were located by counterstaining with Hoechst 33258 for 7 minutes. Images were captured using a Zeiss epifluorescence microscope with a CCD camera.

The small artery densities (α-SMA positive cells surrounding the whole circumference of the vessel) were measured and images were taken from 10 randomly-selected areas of adductor magnus muscle (200× magnification) in each sample, and blinded quantification was performed in triplicate by manually counting within each section; values from five sections were then averaged and expressed as arteriole density per $mm^2$.

Bone-Marrow-Derived Mesenchymal Stem Cells (BM-MSCs) Isolation, Cell Culture, and Treatments Primary rat BM-MSCs were isolated from femur of male Sprague-Dawley rats (300-450 g). Femora were aseptically removed and dissected free of adhering tissues, and then the marrow cavities were flushed by injection of DMEM medium. Collected bone marrow cells were incubated in a 100×15-mm Petri dish in DMEM medium supplemented with 10% FBS, 100 U/ml penicillin, and 100 µg/ml streptomycin for 2 weeks in 5% $CO_2$ at 37° C. The medium was replaced every 2 to 3 days. For passage, near-confluent cells were detached by 0.25% trypsin and then $2 \times 10^5$ subcultured cells were seeded in a well of 6-well plate and further cultured in the 10% FBS-DMEM. Before treatment, cells were starved for 12 hours in DMEM supplemented with 1% FBS followed by treatment with 50 nM PEDF-derived peptide (29-mer or 20-mer) in fresh 1% FBS-DMEM for either 24 or 48 hours.

RNA Extraction and Reverse Transcription-Polymerase Chain Reaction

The total RNA was extracted from cells using TRIzol and treated with RNase-free DNase I (Qiagen, Santa Clarita, Calif.) to remove genomic DNA and then purified with an RNA purification kit (Dynabeads). 1 µg of total RNA retrieved from BM-MSCs was reverse-transcribed into cDNA by 200 units of expand Reverse-Transcriptase (Roche, Mannheim, Germany) in 20 µl of reaction buffer containing 0.25 µg of random primers and 0.8 mM dNTPs at 42° C. for 1 hour. 2 µl of the cDNA was used as templates in subsequent PCR reaction.

PCR was performed using a reaction volume of 30 µl containing 15 µl of EconoTaq® PLUS GREEN 2× Master Mix (Lucigen® Corp.), 1 µM of each primer and 2 µl of template DNA. cDNA was synthesized in an 18-22 cycle amplification reaction (denaturation, 20 s, 94° C.; annealing, 30 s, 57° C.; and polymerization, 40 s, 72° C.). Cycle number for each primer set was established to be in the linear range of amplification. The primer set for the amplification of rat Tenomodulin gene (TNMD; accession number: NM_022290) included a forward primer of AGAATGAGCAATGGGTGGTC (SEQ ID No: 10) and a reverse primer of CTCGACCTCCTTGGTAGCAG (SEQ ID No: 11), and PCR products of about 240 bp were observed. Analysis of rat glyceraldehyde 3-phosphate dehydrogenase (GAPDH; accession number: X02231.1) gene was used as a housekeeping gene for the normalization of the expression level. For the amplification of GAPDH gene, the primer set including a forward primer of AGACAGCCGCATCTTCTTGT (SEQ ID No: 12) and a reverse primer of CTTGCCGTGGGTAGAGTCAT (SEQ ID No: 13) was used, and PCR products of about 207 bp were observed.

The PCR products were electrophoresed in a 2% agarose gel containing ethidium bromide and visualized by UV illumination. The intensities of the PCR products were quantified densitometrically using a FUJI LAS-3000 system and Multi Gauge Ver. 1.01 software (Fujifilm, Tokyo, Japan).

Statistics

Results were expressed as the mean±standard error of the mean (SEM). One-way ANOVA was used for statistical comparisons. $P<0.05$ was considered significant, unless otherwise specified.

Example 1

Sustained Release of PEDF Peptides from Alginate Gel

To determine the release kinetics of 29-mer and 20mer, 100 µg of FITC-conjugated PEDF peptide was mixed with 100 µL alginate solution, and then hydrogels were prepared as set forth in the "Materials and Methods" section. Thereafter, 100 mg hydrogel was incubated in 1.5 ml of PBS (pH 7.4) in microcentrifuge tube and placed in an orbital shaking incubator over a 6-day period at 37° C. The tube was centrifuged at each predetermined time point and then 200 µL of supernatant was removed and stored at −80° C. for further analysis, and 200 µL of fresh PBS was added to the tube to replace the supernatant withdrawn. The concentration of FITC-conjugated PEDF peptide present in the collected supernatants was determined using a fluorimeter in 96-well format. A known non-encapsulated FITC-peptide was used to generate a standard curve. Triplicate data were used for analysis.

The results of the assay, as summarized in FIG. 1, revealed that the embedded PEDF peptides were released in a sustained manner over a 6-day period. Specifically, approximately 48% of 29-mer and 35% of 20-mer peptide remained in the alginate gel matrix after 24 hours. Most of the 29-mer peptides (90%) were released within the first 4 days, after which time the release rate decreased significantly thereby resulting in a plateau of the cumulative release curve. The 20-mer peptides were released in a slightly faster rate in which about 90% of the loaded 20-mer was released in the first 3 days.

Example 2

Sustained Release of PEDF Peptides Reduces Ischemic Damages

Ischemic muscle injury typically leads to necrosis and loss of tissue and function. Hence, ischemic animal model was employed in the present examples to investigate the possibility that the local delivery of the PEDF peptide/alginate gel formulation (herein "the sustained-release formulation") may promote the recovery of tissue or organ functions in the case of tissue or organ damages. Various conditions associated with ischemic damages, such as, limb perfusion, tissue necrosis, arteriogenesis, and neovessel sprouting, were analyzed in the examples as follows.

6-week-old female C57BL/6 wild-type mice were anesthetized by an intraperitoneal injection of a mixture of zoletil (6 mg/kg) and xylazine (3 mg/kg). Hair was removed from the hindquarter with a depilating cream. To establish hindlimb ischemia, unilateral external iliac and femoral arteries and veins were ligated, cut, and excised. After surgery, the mice were randomly assigned to several experimental groups (n=6, each group) and treated as follows. In the blank control group, the mice were treated with 50 µl of blank alginate gel, whereas in the bolus control group, the mice received the bolus formulation containing 29-mer. In the PEDF peptide/alginate gel treatment groups, the mice received 50 µl of the sustained-release formulation, which comprised either 29-mer, 24-mer, or 20-mer. Additionally, in a PEDF 18-mer control group, mice were treated with a sustained-release formulation containing a PEDF 18-mer peptide. Treatments were applied by way of a single intramuscular injection to the gracilis muscle immediately after femoral artery and vein excision operation. The incision was closed after the wound was irrigated with sterile saline.

Example 2.1

Sustained Release of PEDF Peptides Enhances Limb Perfusion

Figure 2:
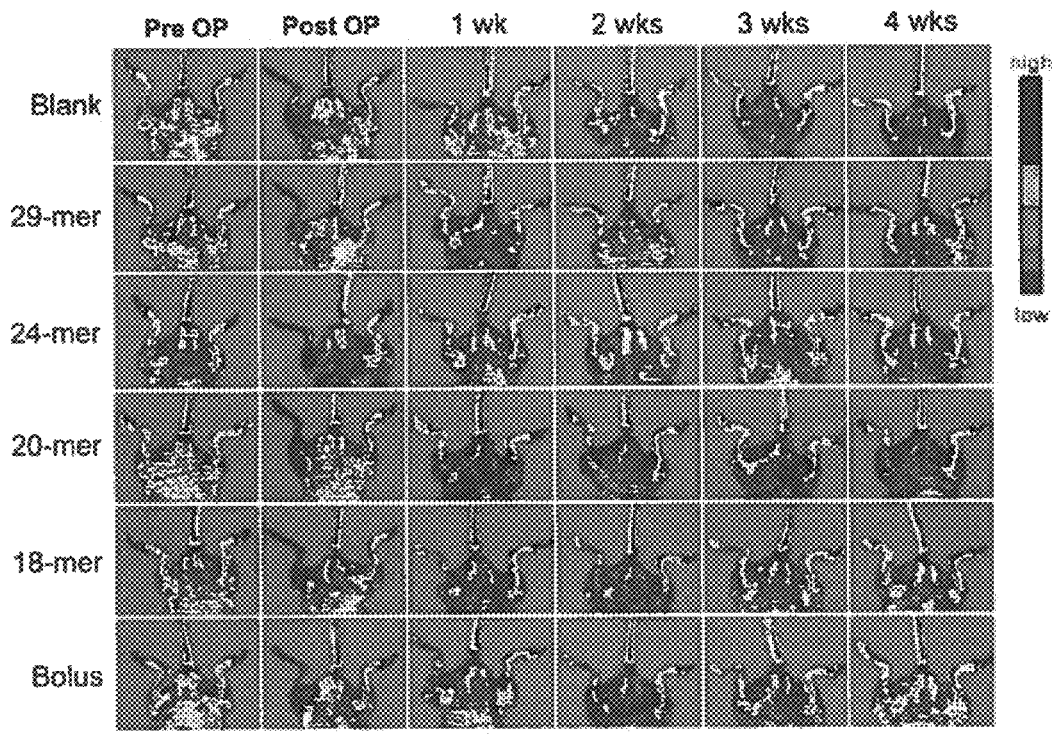
FIG. 2 provides representative LDPI images illustrating the blood perfusion of ischemic hindlimbs over a time period of 4 weeks.

A laser Doppler perfusion imaging (LDPI) analyzer (Moor Instruments, USA) was used to quantify hindlimb blood perfusion before surgery (pre OP), immediately after surgery (post OP), and over time after surgery. To minimize vasoconstriction by anesthetic heat loss, animals were kept on a heating plate at 37° C. for 5 min before measurement. Representative LDPI images illustrating the blood perfusion of ischemic hindlimbs over a time period of 4 weeks were provided in FIG. 2 in which dark blue color represents low blood flow. Blood perfusion is expressed as LDPI index representing the ratio of operated (ischemic) versus non-operated (non-ischemic) limb blood flow of the same mouse, and the results were summarized in FIG. 3 and Table 1 (n 6). Blood flow was displayed as changes in the laser frequency, represented by different color pixels.

TABLE 1

| | Ischemic/Non-ischemic Perfusion Ratio (%) | | | | | |
|---|---|---|---|---|---|---|
| Treatment | Pre OP | Post OP | 7 days | 14 days | 21 days | 28 days |
| Blank  | 99.4 ± 1.5  | 8.1 ± 0.87 | 30.6 ± 1.9   | 28.4 ± 3.9   | 46.3 ± 3.8  | 50.0 ± 6.5 |
| Bolus  | 112.9 ± 6.2 | 9.0 ± 0.80 | 22.9 ± 4.6   | 31.6 ± 2.1   | 44.1 ± 8.4  | 55.3 ±± 2.8 |
| 18-mer | 104.5 ± 2.5 | 7.5 ± 0.67 | 23.8 ± 4.5   | 30.3 ± 0.94  | 46.8 ± 4.3  | 52.8 ± 7.4 |
| 29-mer | 108.2 ± 8.8 | 7.0 ± 3.1  | 44.8 ± 2.0*  | 77.6 ± 6.8*  | 101 ± 7.0*  | 105 ± 4.8* |
| 24-mer | 91.5 ± 5.6  | 8.0 ± 0.03 | 53.1 ± 0.37* | 67.2 ± 5.8*  | 86.1 ± 5.9* | 91.8 ± 5.5* |
| 20-mer | 98.0 ± 7.8  | 4.6 ± 0.64 | 43.3 ± 7.2*  | 60.0 ± 9.0*  | 75.5 ± 5.2* | 92.7 ± 3.0* |

*$P < 0.05$ versus blank control.

Figure 3:
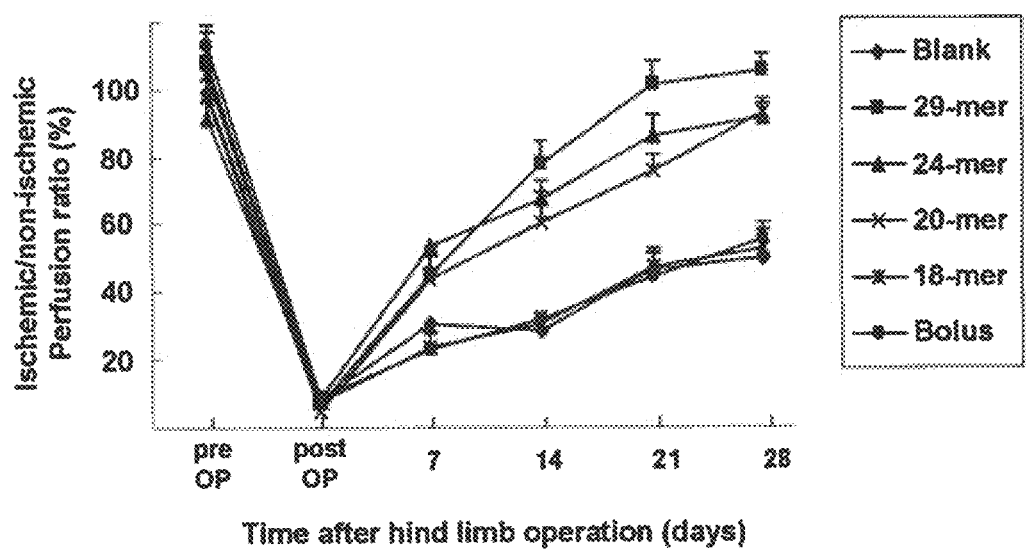
FIG. 3 illustrates the blood perfusion analysis of mice hindlimbs treated with blank alginate gel, sustained-release formulation containing 29-mer, 24-mer, 20-mer, or 18-mer, and bolus formulation containing 29-mer. The results are presented as the means±standard deviation for three separate experiments; n≥6. *P<0.05 versus blank control.

As illustrated in FIG. 3, after the surgery, the regional blood flow (post OP) was immediately reduced to about 8% of the non-ischemic limb of the same animal in all groups, as expected. Blank (alginate gel-only) control led to a slow increase in reperfusion over time. It should be noted that results from the bolus delivery was similar to that of the blank control, indicating that sustained release of PEDF peptides is essential for exerting its protective effect. Also, mice treated with sustained-release formulation containing the control 18-mer peptide did not exhibit improved blood perfusion as compared with that of the blank control or the bolus control; suggesting that the 18-mer peptide is ineffective in treating ischemia. In contrast, the present PEDF treatments significantly improved blood perfusion over that of the blank, bolus, and PEDF 18-mer control groups. In particular, animals treated with sustained formulations containing 29-mer, 24-mer, or 20-mer exhibited a marked increase in blood flow (at least about 60% of normal limbs) starting around the second weeks after the surgery. By four weeks after the surgery, the perfusion in animals treated with 29-mer, 24-mer, and 20-mer delivered with the sustained-release formulations lead to a final recovery of, respectively, 105%, 92%, and 93% of normal limbs, as compared with 50% in the blank control and 55% in the bolus control.

Example 2.2

Sustained Release of PEDF Peptides Prevents Ischemia-Induced Tissue Necrosis

In most hindlimb ischemia models, tissue necrosis generally occurs in the muscles below the knee. For example, tibialis anterior muscle, which is distant to the gracilis muscle where the treatment was administered, often undergoes extensive necrosis with regeneration after femoral artery excision. The intensity of Masson's trichrome blue color staining depended on the content of collagen fibers in the investigated tissue, and fibrosis is the result of necrosis. Hence, two weeks and seven weeks after the surgery and the treatment, samples from the tibialis anterior muscle were analyzed by Masson's trichrome staining to assess the degree of fibrosis and hence necrosis. Results from representative samples are illustrated in FIGS. 4A and 4B.

Figure 4A:
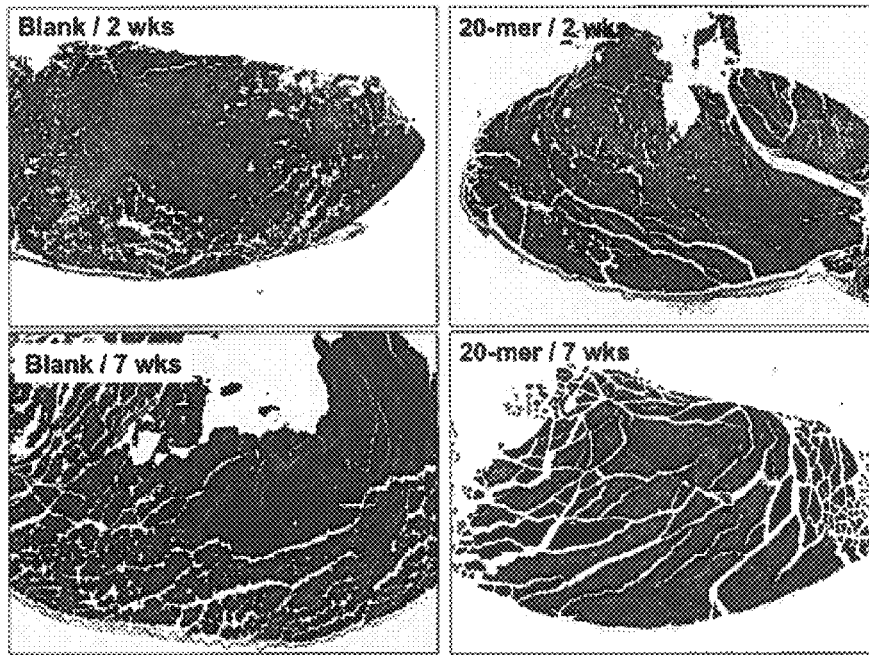
FIG. 4A provides representative photographs from tibialis muscle specimens stained by Masson trichrome (original magnification, ×40), and FIG. 4B provides representative photographs from the same specimens at higher magnification to highlight the extent of necrosis after surgical induction of hindlimb ischemia for 2 and 7 weeks (original magnification, ×200).
Figure 4B:
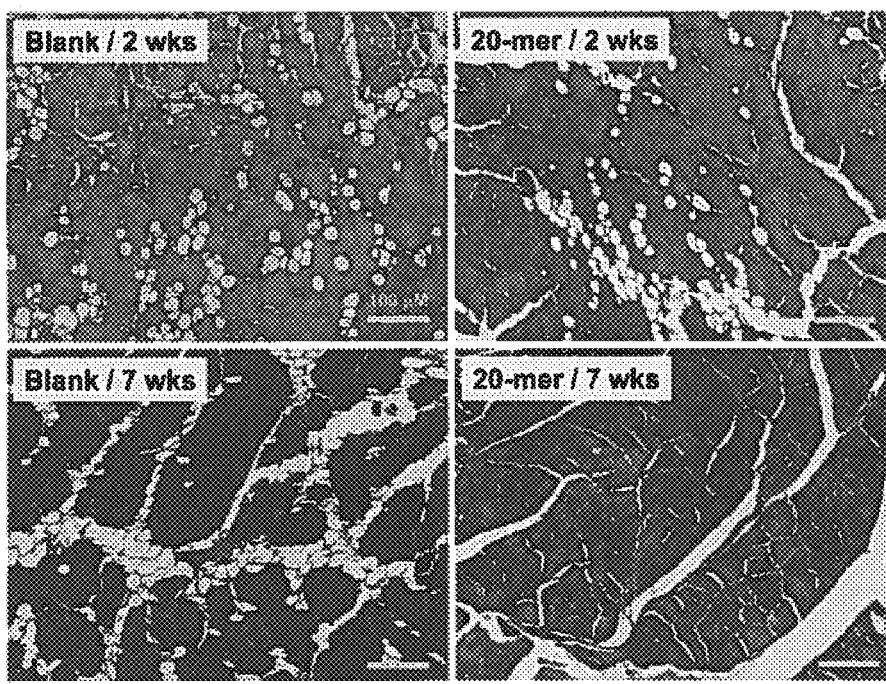

As depicted in FIG. 4A, at the second week after the surgery, muscle tissue from the blank control groups exhibited extensive fibrosis (indicated by the blue stain), whereas muscle tissue treated with the present sustained-release formulation exhibited a relatively smaller fibrosis region. Note also in FIG. 4A, at week 7 post-surgery, the treatment with the present sustained-release formulation effectively reduced the areas of necrosis and fibrosis thereby achieved a complete recovery of muscle tissue.

After ischemic injury, muscle fiber regeneration is achieved by proliferation of satellite cells. The newly formed muscle fiber is marked by centrally located nuclei. Also, the necrotic area is evidenced by necrotic myofibers exhibiting a pale eosinophilic cytoplasm with oedema and a loss of peripheral nuclei. As revealed in FIG. 4B, two weeks after the surgery, the regeneration of myofibers with centrally located nuclei was more significant in mice treated with the present sustained-release formulation than that in mice treated with the blank control. Still referring to the upper panels of FIG. 4B, the large pale red area in the sample from the blank control group, as compared with the sample from the 20-mer treatment group, also suggested that the present sustained-release formulation was effective in preventing necrosis. At week 7 post-surgery, small bundles of muscle fiber with intersperse fat droplet remained in 15% of muscle area in tibialis anterior muscle in groups treated with blank control (FIG. 4B; lower left panel).

Statistical analyses regarding injured area (necrotic area+fibrotic area) and numbers of centrally nucleated fibers were also performed at two weeks after the surgery, and the results were summarized in Table 2. The injured area is expressed as the percent of total stained area (%), and the centrally nucleated fibers is expressed as the total number of muscle fibers counted (%).

The data summarized in Table 2 revealed that the injection of the present sustained-release formulation may substantially reduce tissue injury as compared with that of blank or bolus controls. Specifically, the injured areas of the PEDF treatment groups were reduced to about 45-48% of those of the blank or bolus control group. Also, these data suggested that the treatment with 29-mer, 24-mer, or 20-mer formulation resulted in an increase (about 3-3.7-fold) in the number of centrally nucleated fibers in tibialis anterior muscle, as compared with that of blank or bolus control.

TABLE 2

| Treatment | Injured Area (%) | Centrally nucleated fibers (%) |
|---|---|---|
| Blank | 81.0 ± 3.3 | 19.5 ± 2.2 |
| Bolus | 80.1 ± 4.1 | 20.2 ± 3.2 |
| 18-mer | 78.5 ± 5.1 | 20.5 ± 3.3 |
| 29-mer | 39.5 ± 4.2* | 72.5 ± 5.2† |
| 24-mer | 36.8 ± 5.5* | 67.8 ± 5.3† |
| 20-mer | 38.0 ± 5.2* | 61.2 ± 5.8† |

*$P < 0.001$ versus blank control.
†$P < 0.02$ versus blank control.

In sum, results in Example 2.2 suggested that the treatment with the present sustained formulation containing either 29-mer, 24-mer, or 20-mer may prevent necrosis and fibrosis induced by ischemia, and thereby may improve the recovery of muscle tissue. Also, the increase of recovery of tibialis muscle in mice treated with the present sustained-release formulation provides additional evidence to support its effect on the promotion of blood perfusion in ischemic limb (Example 2.1 above).

Example 2.3

Sustained Release of PEDF Peptides Stimulates Arteriogenesis that Supplements Ischemic Tissue with Collateral Circulation In the case of acute occlusion of a major artery (such as coronary artery or femoral artery), pre-existing arteriolar connections can be recruited to bypass the site of occlusion. This process is termed arteriogenesis which differs in many aspects from angiogenesis. From the anatomical aspect, these pre-existing collateral arteries, unlike capillaries formed during angiogenesis, are microvascular, thin-walled conduits that are composed of an endothelial lining, an internal elastic lamina, and one or two layers of smooth muscle cells. Under normal conditions, these endogenous pre-existing thin-walled arterioles may not be utilized to provide perfusion. However, following occlusion of a major artery, these vessels can dramatically increase their lumen by growth, bypassing the site of occlusion so as to provide enhanced perfusion to the jeopardized ischemic regions. During chronic or acute occlusion of a major artery, collateral arteries may ameliorate the ensuing detrimental effects in many regions of the body (hindlimb, heart, brain, kidney, etc.). It is important to recognize that arteriogenesis is not a simple process of passive dilatation of pre-existing collateral arteries; rather, it is associated with active proliferation and remodeling by growth of pre-existing arteriolar connections into true collateral arteries. It is established that vessel radius is the dominant influence on blood flow, and hence, the collateral arteries, after adaptive growth, are capable of conducting relatively large blood volumes per unit of time. Therefore, stimulation of arteriogenesis is probably the more efficient mechanism for the survival of ischemic limbs or internal organs such as heart and brain, in comparison to angiogenesis. In contrast, angiogenesis is the formation of capillaries composed of endothelial cells from the pre-existing vessels; these capillaries are fruitless in proving higher profusion to the damaged ischemic region. Thus, the increase in blood flow to the potentially ischemic tissue, as caused by the development of two or three large collateral arteries, cannot be equaled by newly formed capillaries, however numerous.

Figure 5:
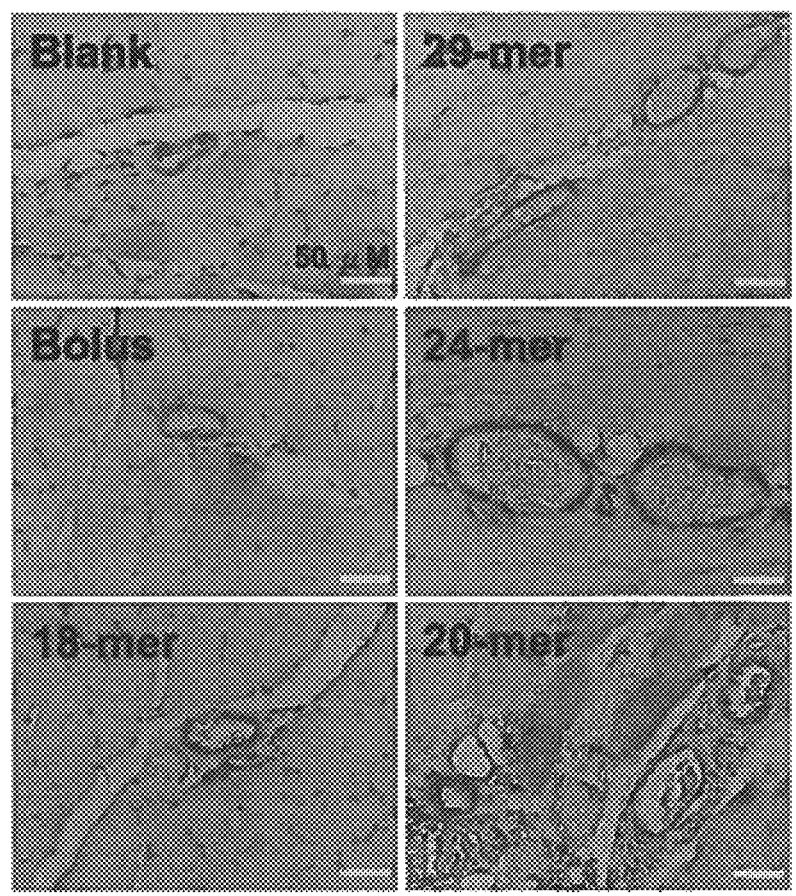
FIG. 5 provides representative immunostained images of arterioles in adductor magnus muscle after 2 weeks of ischemia. Arterioles were labeled with anti-α-SMA (brown) and nuclei were labeled with hematoxylin.

To investigate the arteriogenic effect of the present sustained-release formulation, adductor magnus muscles (located at the same level as femoral artery excision and in which arteriogenesis responsible for establishing collateral circulation is expected to be found) were harvested from animals in each experimental condition, two weeks after the surgery. Arterioles in muscle cross sections were identified by immunohistological staining for vascular smooth muscle cells (α-SMA; brown), and nuclei were labeled with hematoxylin; representative photographs were provided in FIG. 5. Quantitative analysis was also performed and the results were summarized in Table 3, and the data were expressed as α-SMA-positive arterioles per $mm^2$ in the peri-injury region.

TABLE 3

| Treatment | Arteriole Density per $mm^2$ |
|---|---|
| Blank | 3.3 ± 0.88 |
| Bolus | 3.7 ± 1.2 |
| 18-mer | 4.0 ± 0.58 |
| 29-mer | 11.7 ± 1.5* |
| 24-mer | 10.0 ± 0.58* |
| 20-mer | 10.7 ± 1.2* |

*$P < 0.001$ versus blank control.

These data revealed that the administration of the present sustained-release formulation increased arteriole density in adductor magnus muscle adjacent to the femoral artery excision, as compared with that of the blank and bolus control groups. Therefore, the sustained release of PEDF peptides provides arteriogenic activity to establish collateral circulation after the acute disruption of blood supply. The dramatically increase the lumen of these vessels by growth provides enhanced perfusion to the jeopardized ischemic regions. This well-developed collateral network leads to the recovery from ischemic events.

Example 2.4

PEDF Peptide Stimulate Ex Vivo Neovessel Sprouting

Figure 6:
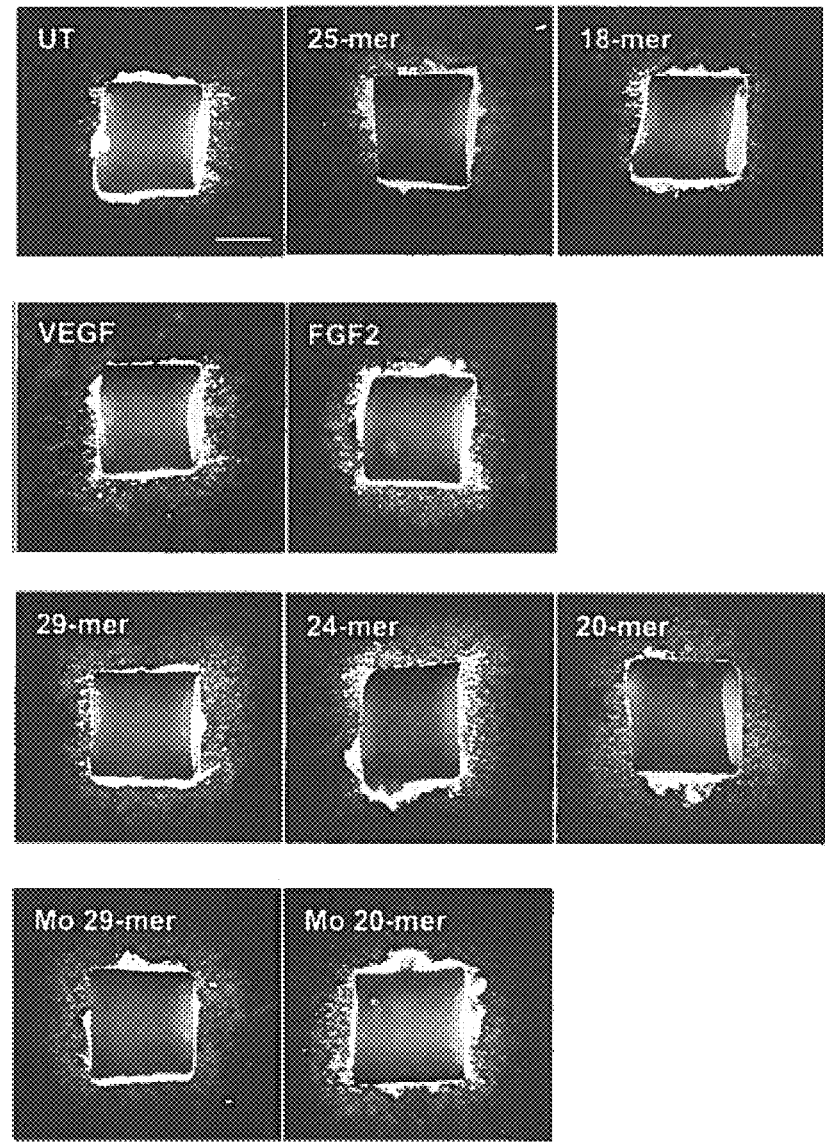
FIG. 6 provides representative photographs of aortic ring explants cultured for 4 days in either basal MCDB131 medium (untreated control) or medium supplemented with known angiogenic factors (FGF2 or VEGF), the control PEDF peptides (25-mer or 18-mer), or the PEDF peptides according to embodiments of the present disclosure (29-mer, 24-mer, 20-mer, Mo 29-mer, or Mo 20-mer).

To further confirm the neovessel development promoted by PEDF peptides, rat aortic ring sprouting assay was performed. Thoracic aortas were removed from euthanized rats and gently stripped of peri-aortic fibroadipose tissue. Aortas were sectioned into about 2-mm length rings, which were then embedded in a growth factor-reduced Matrigel. Gels containing the aortic rings were polymerized in 12-well plates incubated at 37° C. for 30 minutes. 1 ml of MCDB131 medium supplemented with 100 units/ml penicillin and 100 ng/ml streptomycin, 1% FBS, and a supplemental agent (50 ng/ml VEGF-A, 20 ng/ml FGF-2, or 50 ng/ml 29-mer, 24-mer, 20-mer, Mo 29-mer, Mo 20-mer, 25-mer, or 18-mer) were added to the Matrigel-containing explants. The cultures were propagated at 37° C. in a humidified incubator for up to 4 days, with media changes every other day. Neovessel sprouting was assessed until day 4 using an inverted microscope platform (Leica) with bright-field optics; representative photographs were provided in FIG. 6. Quantification of neovessel sprouting was assessed using Image-Pro Plus 6.0 software (Dendrites program). Results were expressed as a fold of untreated aortic ring, as summarized in Table 4. The experiment was repeated in triplicate.

In the untreated control (UT) in which no supplemental factor was administered, minimal neovessel sprouting was observed at day 4. It is also noted that the control PEDF peptides (i.e., 25-mer and 18-mer) did not substantially enhance the neovessel sprouting, compared with the untreated control.

TABLE 4

| Treatment | Neovessel Sprouting Fold |
|---|---|
| Untreated | 1 |
| VEGF | 3.4* |
| FGF2 | 3.5* |
| 18-mer | 0.97 |
| 25-mer | 0.89 |
| 29-mer | 5.6* |
| 24-mer | 6.2* |
| 20-mer | 6.5* |
| Mo 29-mer | 6.1* |
| Mo 20-mer | 6.4* |

*P < 0.02 versus untreated control.

As expected, the well-known angiogenic factors, VEGF and FGF2, induced substantial neovessel sprouting. The neovessel sprouting in samples treated with VEGF and FGF-2 increased for about 3.4-fold and 3.5-fold, respectively; as compared to that of the UT control.

Figure 7:
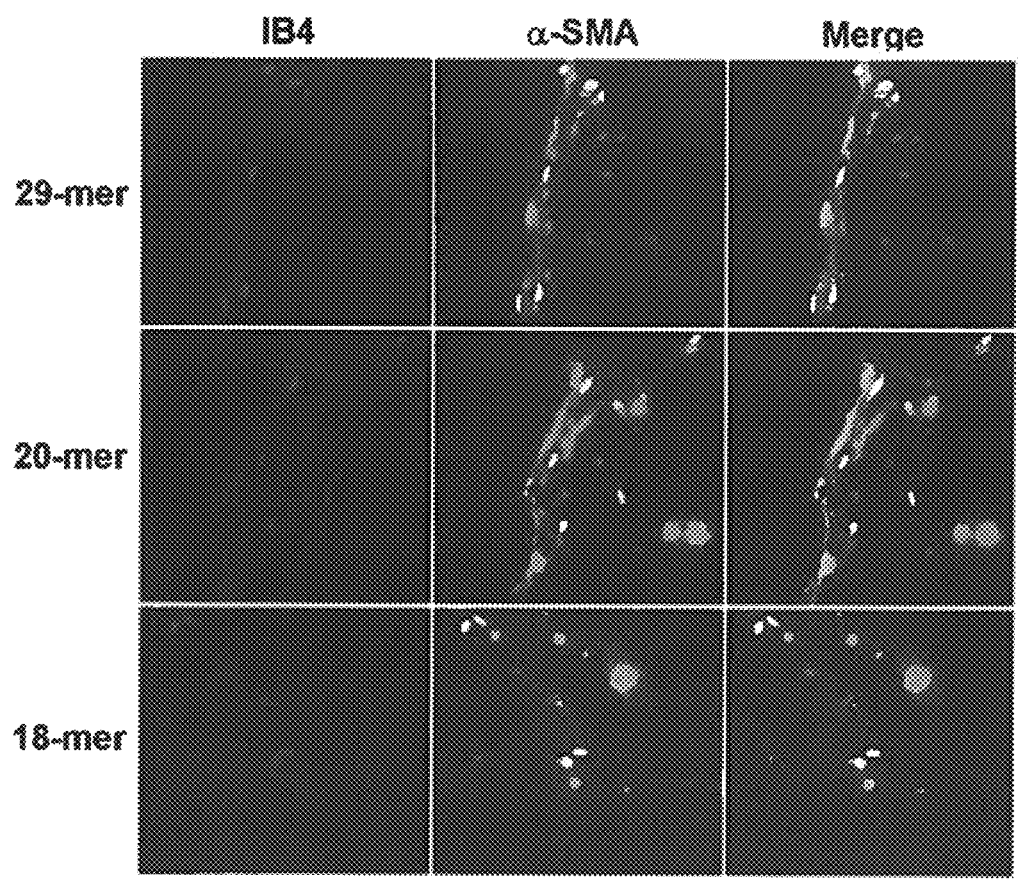
FIG. 7 provides representative dual-immunostained images illustrating vascular smooth muscle cells (vSMCs) outgrowth from aortic rings cultured in medium supplemented with PEDF peptide (29-mer, 20-mer and 18-mer), in which endothelial cells were detected by Alexa Fluor 594-labeled isolectin B4 (IB4; red; left panel) and vSMCs were labeled with anti-α-SMA (green; middle panel). Merged images are located on the right (yellow). Nuclei were visualized with Hoechst 33258 staining. Original magnification, ×400. Images are representative of four independent experiments.

The data in Table 4 also indicated that the present PEDF peptides (including 29-mer, 24-mer, 20-mer, Mo 29-mer, and Mo 20-mer) stimulated more neovessel sprouting than either VEGF or FGF2. These neovessels were examined by dual-staining immunofluorescence assay for α-smooth muscle actin (a marker of arteriole wall smooth muscle cell (SMC)) and isolectin B4 (IB4, a marker of endothelial cells), and representative photographs were provided in FIG. 7. As could be seen in FIG. 7, samples treated with the present PEDF peptide (29-mer or 20-mer) displayed arteriole phenotype with a SMC coating. In contrast, the formation of endothelial tube and SMC proliferation was barely detected upon treatment with PEDF 18-mer. This result indicated that PEDF peptides according to embodiments of the present disclosure can stimulate neovessel formation beyond the angiogenesis of capillary which only contains endothelial cells in culture. It thus supports the notion that the present PEDF peptides stimulate arteriogenesis in vivo.

In conclusion, data presented in Example 2 (including Examples 2.1 to 2.4) demonstrated that the present PEDF peptides were effective in enhancing limb perfusion, reducing tissue necrosis and fibrosis, and promoting arteriogenesis and neovessel sprouting, and hence, the administration of the PEDF peptides (in particular, the sustained-release formulation containing either of the PEDF peptides) would reduce ischemic damages and facilitate the structural and functional recoveries of the tissue or organ. It should be noted that it has been established that a 34-mer fragment of PEDF (residues 44-77) has anti-angiogenic properties, and a 44-mer fragment of PEDF (residues 78-121) has neurotrophic properties. However, the present disclosure is the first to confirm that short PEDF fragments (at least the 29-mer, 24-mer, 20-mer, Mo 29-mer, and Mo 20-mer) exhibit an arteriogenic activity.

Example 3

Sustained Release of PEDF Peptides Promotes Muscle Regeneration

To investigate the effects of the present PEDF peptides on muscle regeneration, a rat myonecrosis model of a single injection of bupivacaine into the soleus muscle was employed. Adult 10-week-old male Sprague-Dawley rats (initial body weight=312±11 g) were anesthetized by an intraperitoneal injection of a xylazine (10 mg/kg). Then, the soleus muscle was injured by unilaterally injecting 0.5 ml bupivacaine (AstraZeneca) with a disposable syringe with a 26-gauge needle. Briefly, the needle was inserted into the distal portion of the soleus muscle and then receded longitudinally to the proximal portion accompanying evenly bupivacaine solution injection. The solution was then injected throughout the entire length of the muscle as the needle was slowly withdrawn.

After bupivacaine injection, rats were divided equally (n=10/group) into four experimental groups and treated as follows. In the blank control group, the mice were treated with 50 μl of blank alginate gel. In the treatments groups, the mice received 50 μl of the sustained-release formulation (29-mer or 20-mer). The mice in the bolus control group received the bolus formulation (29-mer). Treatments were applied by way of a single intramuscular injection to the soleus muscle immediately after the bupivacaine perfusion.

At day 4 after bupivacaine injection, histology of soleus muscle cross section consisted of general necrosis with disintegrating myofibers and abundant infiltrating inflammatory cells occupying a great major part of the soleus muscle (photographs not shown). Only in the peripheral were some muscle fibers with relative normal structure remained. The degrees of muscle fiber necrosis were the same in blank control group and peptide treatment group. This result indicated that the necrosis levels induced by bupivacaine in different groups were substantially the same.

Example 3.1

Sustained Release of PEDF Peptides Promotes Cell Proliferation

Muscle regeneration involves proliferation of muscle fibers, or muscle cells. The muscle fiber proliferation was assayed by the incorporation of BrdU in the proliferating nuclei. Satellite cells proliferation is the key step of muscle regeneration. Hence, the soleus muscle specimens were also stained for satellite cell marker, Pax7, so as to investigate the muscle regeneration activity. Detailed assay procedures are as described in "Materials and Methods." The level of BrdU-positive cells was expressed as labeling index (%), which was computed as the number of labeled cells divided by the total number of cells. The labeling index (%) of Pax7-positive cells was computed as the number of labeled cells divided by the total number of cells with nuclei. Quantitative results were evaluated from 6 sections per muscle section and 10 mice at each group, and were summarized in Table 5.

TABLE 5

| Treatment | BrdU Labeling Index (%) | Pax7 Labeling Index (%) |
|---|---|---|
| Blank | 4.2 ± 0.9 | 2.0 ± 0.71 |
| Bolus | 4.4 ± 1.4 | 2.6 ± 0.68 |
| 29-mer | 15.4 ± 1.7 | 16.2 ± 2.0 |
| 20-mer | 13.6 ± 3.0 | 14.6 ± 1.9 |

These results revealed that the numbers of BrdU-positive cells in wounds treated with the 29-mer- or 20-mer-containing sustained-release formulation were significantly increased, as compared with wounds treated with the blank or bolus control. Regarding the proliferative activity of satellite cells, the data revealed that the present sustained-release formulations lead to higher percentages of Pax7-positive cells as compared with blank and bolus controls. Together, these data suggested that the administration of the present sustained-release formulations enhances the proliferative activities of muscle fibers and/or satellite cells, which in turn may promote the muscle to regenerate.

Example 3.2

Sustained Release of PEDF Peptides Promotes Muscle Fiber Regeneration

In the process of muscle regeneration, newly generated muscle fibers typically contain central located nuclei. Hence, the percentage of such centrally nucleated muscle fibers is also an indicator of the regenerative activity of muscle. Statistical analysis regarding the percentage of centrally nucleated fibers was performed at day 7 after the bupivacaine injection, and the results were summarized in Table 6.

TABLE 6

| Treatment | Centrally nucleated fibers (%) |
|---|---|
| Blank | 11.0 ± 1.7 |
| Bolus | 13.8 ± 2.2 |
| 29-mer | 75.2 ± 7.0 |
| 20-mer | 63.3 ± 7.4 |

As could be seen in Table 6, there were higher percentages of muscle fibers containing centrally located nuclei in animals treated with the 29-mer- or 20-mer-containing sustained-release formulation, as compared with that of blank or bolus control groups. These results indicated that the administration of the present sustained-release formulations was effective in promoting muscle regeneration.

Figure 8:
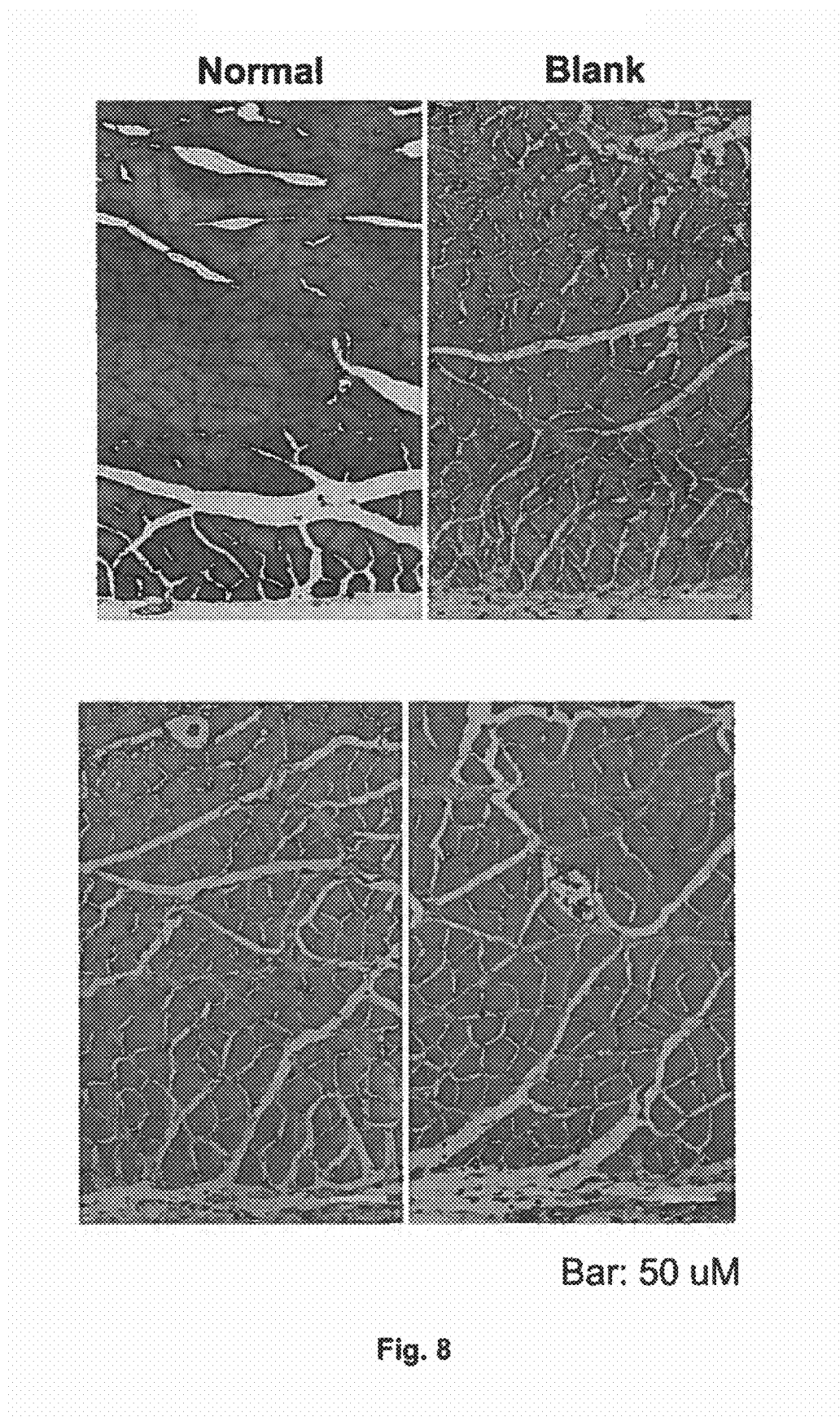
FIG. 8 provides representative photographs from soleus muscle specimens stained by H&E at day 14 following bupivacaine injection.

Also, at 14 days after the bupivacaine injection, necrotic myofibers were replaced by newly formed myotubes in soleus muscle in all experimental groups. However, a number of centrally nucleated fibers remained in regenerating muscles treated with blank or bolus control (FIG. 8), suggesting an incomplete muscle regeneration. In contrast, muscle sections from animals treated with the sustained-release formulation containing 29-mer or 20-mer exhibited much less centrally nucleated fibers. Together, these data indicated that the muscle fiber regeneration was facilitated by the sustained release of the PEDF peptides.

Example 3.3

Figure 9:
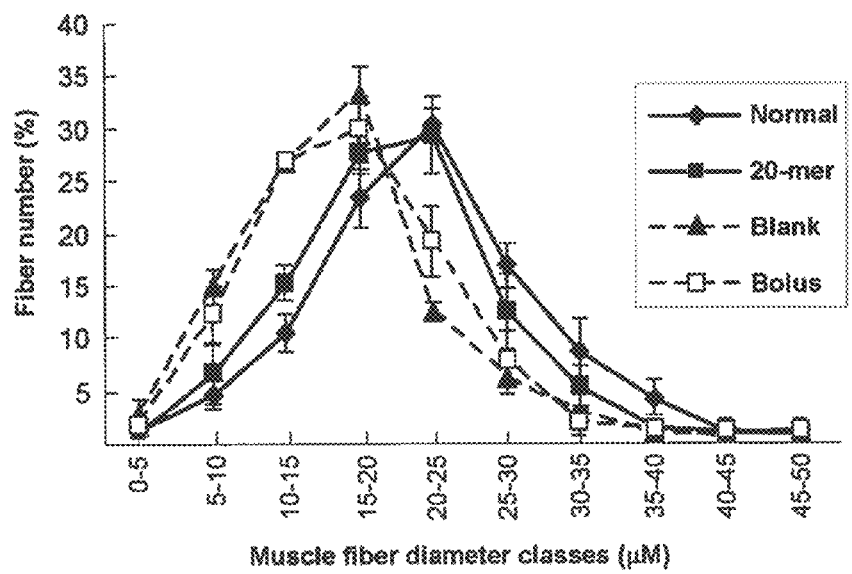
FIG. 9 is a diagram illustrating muscle fiber size distributions of muscles from animals in various experimental conditions.

Sustained Release of PEDF Peptides Promotes Maturation of Regenerated Muscle Fiber In the later stage of muscle regeneration, newly generated muscle fibers start to gain size. Muscle specimens were collected at 14 days after injury, and respective fiber diameters were measured in accordance with the procedure set forth in the section of "Materials and Methods." Results were summarized in FIG. 9.

On average, diameters of muscle fibers from animals treated with the sustained-release formulation containing 29-mer or 20-mer were larger than those from animals in the blank or bolus control group. In addition, the size distribution of the 20-mer-treated muscles was in close resemblance to that of uninjured, intact muscles. Specifically, about 56.6% of muscle fibers from animals treated with 20-mer and about 53.2% of intact muscle fibers had a minimal Feret's diameter between 15-25 μm, whereas about 59.6% and about 56.2% of the regenerated fibers from the blank and bolus control groups had minimal Feret's diameters between about 10-20 μm. These data indicated that the administration of the present sustained-release formulation was effective in increasing the mass of the regenerated muscles.

In conclusion, data presented in Example 3 (including Examples 3.1 to 3.3) demonstrated that the present PEDF peptides are effective in promoting the proliferations of muscle fibers and satellite cells, regeneration of muscle fibers, and the maturation of regenerated muscle fibers, and hence, the administration of the PEDF peptides (in particular, the sustained-release formulation containing either of the PEDF peptides) would promote the muscle regeneration process and facilitate the structural and functional recoveries of the muscle tissue. The present disclosure is the first to discover that short PEDF fragments (at least the 29-mer and 20-mer) are capable of promoting muscle regeneration.

Example 4

Sustained Release of PEDF Peptides Promotes Tendon Regeneration

To investigate the effects of the present PEDF peptides on tendon regeneration, a rat model with tendon injury was established as follows. Adult 10-week-old male Sprague-Dawley rats (total n=50; initial body weight=312±11 g) were anesthetized by an intraperitoneal injection of a xylazine (10 mg/kg). Then, the left tendo Achilles injury was created by full-thickness insertion of an 18-gauge needle through tendo Achilles 1 cm proximal to its insertion into the calcaneum. This created a horizontal (transaction) wound which was flanked by intact tendon tissue on both sides to prevent the retraction of severed ends.

The rats were randomly assigned (n=10/group) to five experimental groups and treated as follows. In the blank control group, the mice were treated with 150 μl of blank alginate gel. For the bolus control group, 150 μl of the bolus formulation (29-mer) was administered. In the treatments groups, the mice received 150 μl of the sustained-release formulation (29-mer, 24-mer, or 20-mer). Treatments were injected subcutaneously near tendon lesion immediately after the injury, and the incision was closed after the wound was irrigated with sterile saline.

Example 4.1

Sustained Release of PEDF Peptides Promotes Tendon Healing

Figure 10:
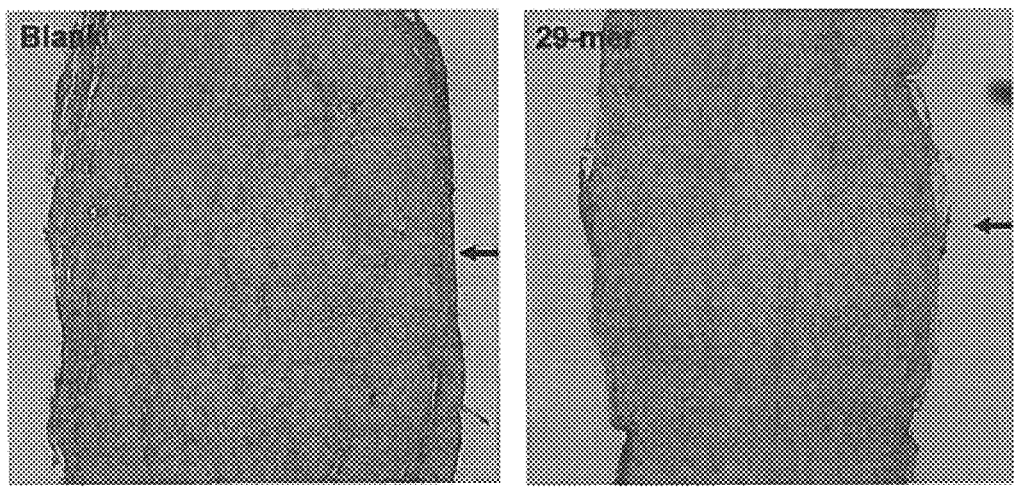
FIG. 10 provides representative photographs illustrating regenerating tissue (↑) at the inner part of tendon at week 3 post-injury. Original magnification, ×100.

Three weeks after tendon injury, histologic analysis was performed to observe the healing of the tendon. Representative photographs were provided in FIG. 10. As could be seen in the upper panel of FIG. 10, in animals treated with blank control, a broad band of disorganized fibrous scar was formed between the two cut ends, and the pink stained collagen bundle was minimal in the scar tissue. In contrast, the cut ends of tendons treated with sustained-release formulation containing 29-mer were healed with much lesser scar tissue as compared with that of the blank control specimen, and the pinkish stain of mature collagen bundle extended into the damaged region of the tendon; also, tendon fibers from the cut ends seemed to joint together in some area (FIG. 10; lower panel). Also, the fibrous tissue in the scar was more organized and in parallel direction in the 29-mer treatment group.

Figure 11:
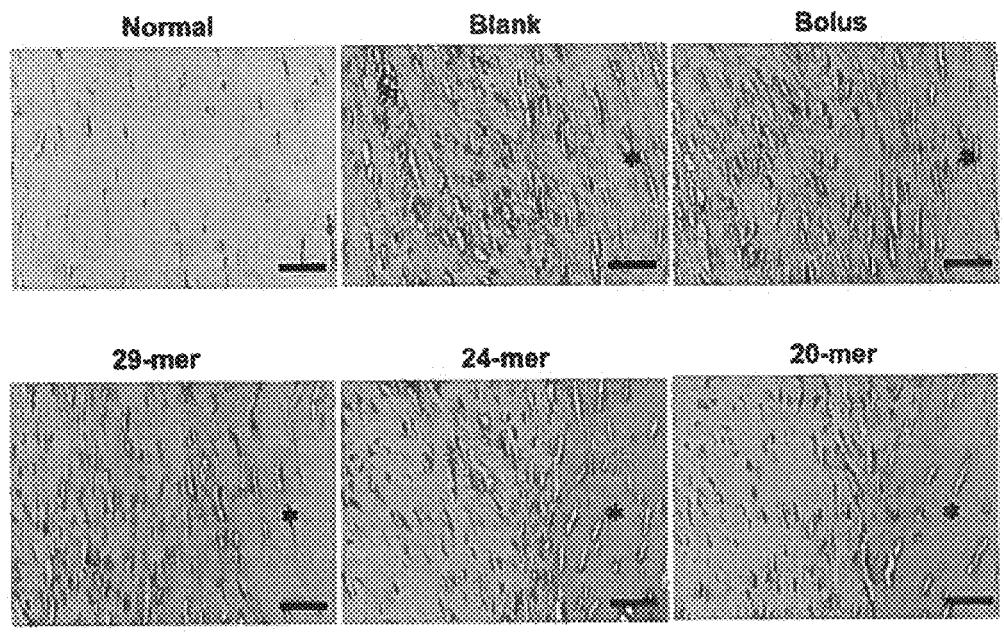
FIG. 11 provides representative photographs of H&E-stained sections of Achillis tendon at 3 weeks after injury. Original magnification, ×400; scale bar=50 μM. Images are representative of three independent experiments.

FIG. 11 provides representative photographs of histologic analysis at higher magnification. Normal tendon had a relative scarcity of cells among the collagen fibers, and the nuclei were mostly elongated. In the blank and bolus control groups, after healing for three weeks, the more abundant presence of fibroblasts (characterized by the presence of round- or spindle-shaped fibroblast-like nuclei) was observed in the tendon, and the newly formed collagen fibers were structurally disorganized (the undamaged tissue was indicated by *). These morphological changes suggested poor healing of the tendon wounds in the blank and bolus control groups.

In contrast, still referring to FIG. 11, in tendons treated with the present sustained-release formulations, the healing regions had thin, elongated nuclei which were morphologically similar to nuclei of mature tenocyte, and the collagen fibers were well organized and parallel to the native tendon (deep pink); suggesting a better healing of the tendon wounds. These results indicated that the tendon wound healing process may benefit from the present sustained-release formulation.

Figure 12:
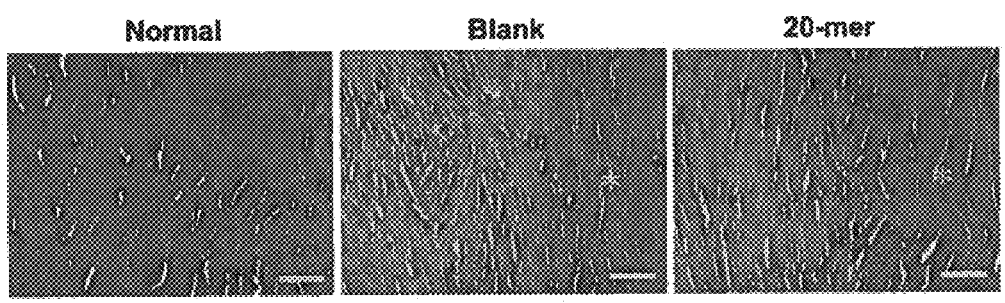
FIG. 12 provides representative photographs of tissue sections stained by Masson's trichrome to highlight the collagen fibers at 3 weeks post-injury. Stars (*) represent the uninjured area in tendon. Original magnification, ×400; scale bar=50 μM. Images are representative of three independent experiments.

Further, Masson trichrome staining was performed to evaluate the structure and organization of collagen fibers, and representative photographs of the specimens were provided in FIG. 12. In the uninjured tendon, collagens fibers were substantially parallel to one another (FIG. 12; left panel). By contrast, the injured tendon treated with blank control had disorganized collagen fibers in the healed region (FIG. 12; middle panel; wound margin marked by *). The injured tendon treated with the present sustained-release formulation, however, had well-organized collagen fibers that were aligned in substantially the same orientation as the uninjured tendon tissue beyond the wound margin (FIG. 12; right panel; wound margin marked by *). These highly oriented and organized collagen fibers suggested a better tendon wound healing effect in animals treated with the present sustained-release formulation.

Quantitative analysis was also performed to assess the percentage of collagen (%) in the regenerated area, and results were summarized in Table 7.

TABLE 7

| Treatment | Collagen in Regenerated Area (%) |
|---|---|
| Blank | 56.0 ± 6.87 |
| Bolus | 58.25 ± 8.84 |
| 29-mer | 88.75 ± 1.89 |
| 24-mer | 85.75 ± 2.56 |
| 20-mer | 82.01 ± 6.55 |

As could be seen in Table 7, animals in the PEDF treatment groups (29-mer, 24-mer or 20-mer) had higher collagen contents in the regenerated area, as compared with those in the blank and bolus control groups. These data suggested that collagen synthesis in the wound region may be promoted by the administration of the present sustained-release formulation.

Figure 13:
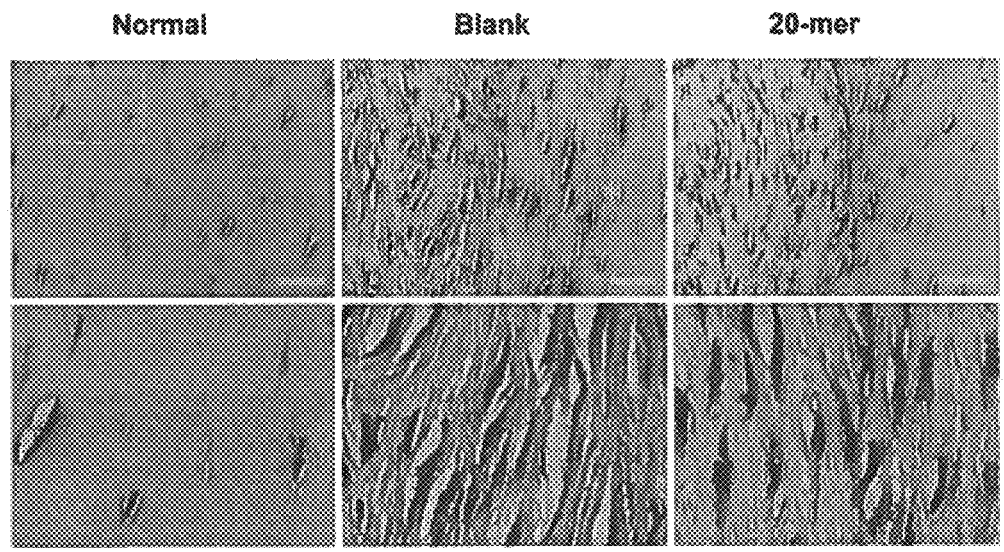
FIG. 13 provides representative immunostained photographs of newly formed type 1 collagen (brown color) in regenerating tendon at 3 weeks after surgery. Nuclei labeled with hematoxylin. Boxed regions are shown at higher magnification below. Scale bar=50 μM. Images are representative of three independent experiments.

The specimens were also subjected to immunostainning of type I collagen, and nuclei were labeled with hematoxylin. Representative photographs were provided in FIG. 13, in which lower panels are photographs of the magnified regions respectively enclosed by dash lines in the upper panels. As could be appreciated, the collagen fibrils in the uninjured tendon were well cross-linked with one another, and hence, they were unlikely to be recognized by the anti-collagen 1A1 antibody. Therefore, only minimal amount of type I collagen (brown stain) was observed in the left panel of FIG. 13. By comparing the photographs of the blank control group (FIG. 13; middle panel) and the PEDF treatment group (FIG. 13; right panel), it was certain that type I collagen (brown) was more abundant in the PEDF treatment groups than in the blank control group.

Collectively, these results suggested that the administration of sustained-release formulation containing the present PEDF peptide would stimulate type 1 collagen synthesis in cells in injured tendon tissues, facilitate collagen deposition in healed tissues, and promote a more organized alignment of collagen fibers, and thereby promote tendon regeneration.

Example 4.2

PEDF Peptides Induces In Vitro TSC Proliferation

It has been reported that during the tendon healing process, tendon stem cells (TSCs) would proliferate and differentiate into tenocytes. To investigate whether present PEDF peptides would induce the proliferation of TSCs in vitro, tendons stem cells were isolated and cultured as described in the "Materials and Methods" section. The purity of TSCs was confirmed by a TSC marker, nucleostemin, as well as the expression of type I collagen by TSCs; together, these analyses indicated a TSC purity of near 100% (data not shown). The proliferation of TSCs was confirmed by BrdU pulse-labeling for 2 hours. Quantitative analysis of the level of BrdU-positive cells was performed as described above, and the results were summarized in Table 8.

TABLE 8

| Treatment | BrdU Labeling Index (%) |
|---|---|
| Control | 9.6 ± 2.1 |
| 29-mer | 31.8 ± 3.6* |
| 24-mer | 29.0 ± 4.6* |
| 20-mer | 33.2 ± 6.6* |
| Mo 29-mer | 33.2 ± 6.6* |
| Mo 20-mer | 31.8 ± 3.1* |

*P < 0.002 versus untreated control cells.

These data revealed that, as compared with TSCs cultured in control medium, TSCs cultured in media containing the present PEDF peptide (29-mer, 24-mer, 20-mer, Mo 29-mer, or Mo 20-mer) were more proliferative. Also, it should be noted that Mo 29-mer and Mo 20-mer are derived from the mouse PEDF peptide, and does not have 100% amino acid sequence identities to the 11-30 amino acid residues of the 39-mer. However, they respectively exhibited similar mitogenic activity to the short PEDF peptides (e.g., 29-mer, 24-mer, and 20-mer) derived from human PEDF.

Example 4.3

Sustained Release of PEDF Peptides Promotes In Vivo TSC Proliferation after Tendon Injury Specimens obtained from animals in different experimental groups of Example 4.1 were stained for nucleostemin (green) to investigate whether in vivo TSC proliferation would be promoted by the present sustained-release formulation during the tendon wound healing process. In quantitative analysis, ten randomly selected microscopic fields in each experimental group were photographed, and the percentage of nucleostemin-positive cells per total cells (counterstained by Hoechst 33258; blue) was calculated. Quantitative results were summarized in Table 9.

TABLE 9

| Treatment | Nucleostemin Labeling Index (%) |
|---|---|
| Blank | 5.8 ± 1.8 |
| Bolus | 5.6 ± 1.4 |
| 29-mer | 16.4 ± 2.9* |

TABLE 9-continued

| Treatment | Nucleostemin Labeling Index (%) |
|---|---|
| 24-mer | 16.8 ± 4.2* |
| 20-mer | 15.0 ± 3.9* |

*P < 0.001 versus blank control.

These data revealed that levels of nucleostemin-positive TSC cells in animals treated with 29-mer, 24-mer, or 20-mer were elevated, as compared with those in the blank and bolus control groups. Taken together, results from Examples 4.1 and 4.3 suggested that the in vivo expansion of TSCs promoted by the administration of the present sustained-release formulation was coincident with the more prominent tendon healing effect, as compared with the native healing process.

Example 4.4

PEDF Peptide Induces Tenocyte-Like Cell Generation from Bone Marrow-Derived Mesenchymal Stem Cells (BM-MSCs)

Figure 14:
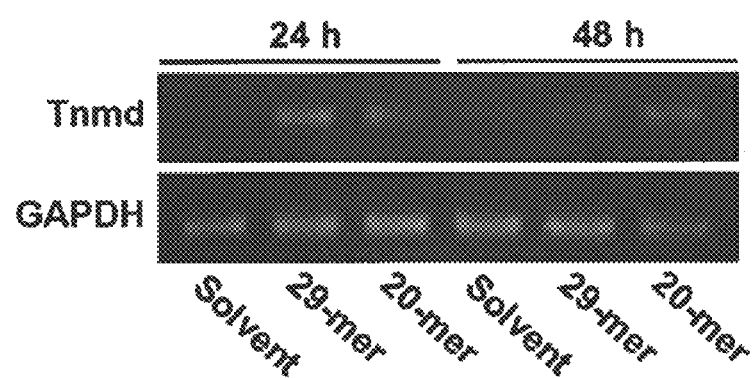
FIG. 14 is a representative gel electrophoresis image illustrating enhanced expression level of tenomodulin (TNMD) gene by the present PEDF peptides (29-mer and 20-mer) according to one working example of the present disclosure. Expression of tenomodulin (TNMD) gene is indicative of BM-MSC differentiation into tenocyte. The image is representative of three independent experiments.

Recently, it is established that adult mesenchymal stem cells (MSCs) could be used to regenerate functional tendons. In this example, BM-MSCs were cultured in a control medium or a medium containing either PEDF 29-mer or 20-mer to investigate the ability of the present PEDF peptides in promoting BM-MSC differentiation into tenocytes. Tenomodulin gene (TNMD) is a gene predominantly expressed in tendons, and is considered as the most reliable phenotypic marker of the tenocytic lineage. Hence, tenocyte differentiation was evaluated based on the expression of TNMD. Representative image from RT-PCR analysis was provided in FIG. 14.

The results revealed that the present PEDF peptide (29-mer or 20-mer) is an effective inducer of tenocyte-like cell differentiation in cultured BM-MSCs. Since the mobilization and differentiation of BM-MSCs is a proposed mechanism of tendon repair in vivo, this observation suggested that the present PEDF peptide may repair tendon damage by promoting the differentiation of BM-MSCs into tenocytes. It also indicated the potential of the present PEDF peptide to facilitate the synthesis of artificial tendons from scaffold matrix culture of BM-MSCs.

In conclusion, data presented in Example 4 (including Examples 4.1 to 4.4) demonstrated that the present PEDF peptides were effective in promoting the synthesis of well-organized collagen (in particular, type one collagen) fibrils and proliferation of tendon stem cells, and hence, the administration of the present PEDF peptides (in particular, the sustained-release formulation containing either of the present PEDF peptides) would promote the tendon regeneration process and facilitate the structural and functional recoveries of the tendon tissue. The present disclosure is the first to discover that short PEDF fragments (at least the 29-mer and 20-mer) are capable of promoting tendon regeneration and BM-MSCs differentiation into tenocytes.

Collectively, results from the preceding examples established that the present synthetic PEDF peptides (such as the 29-mer, 24-mer, 20-mer, Mo 29-mer, and Mo 20-mer) may promote arteriogenesis in or adjacent to the ischemic region, muscle and tendon regeneration in or adjacent to the injured region. Accordingly, the present synthetic PEDF peptides are suitable for use as a therapeutic agent to promote muscle and tendon wound-healing and reduce ischemic damages.

It will be understood that the above description of embodiments is given by way of example only and that various modifications may be made by those with ordinary skill in the art. The above specification, examples, and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A method for promoting muscle regeneration, tendon regeneration, or arteriogenesis in a subject suffering from muscle tissue damage, tendon tissue damage, or ischemia, comprising:
administering an effective amount of a synthetic peptide to the subject at a site in need of treatment, wherein the synthetic peptide consists of an amino acid sequence having 20-39 amino acid residues in length, wherein the amino acid sequence at least includes a sequence selected from the group consisting of SEQ ID NOs: 1-3, 5, 6, 8, and 9.

2. The method for promoting muscle regeneration, tendon regeneration, or arteriogenesis according to claim 1, wherein the synthetic peptide is formulated into a pharmaceutical composition comprising the synthetic peptide and a pharmaceutically acceptable carrier.

3. The method for promoting muscle regeneration, tendon regeneration, or arteriogenesis according to claim 2, wherein the pharmaceutically acceptable carrier is a polymeric material selected from the group consisting of alginate, gelatin, collagen, and poly(lactide-co-glycolide).

4. The method for promoting muscle regeneration, tendon regeneration, or arteriogenesis according to claim 3, wherein the pharmaceutically acceptable carrier is an alginate.

5. The method for promoting muscle regeneration, tendon regeneration, or arteriogenesis according to claim 4, wherein the pharmaceutical composition is formulated in a sustained-release form.

6. The method for promoting muscle regeneration, tendon regeneration, or arteriogenesis according to claim 5, wherein the pharmaceutical composition is formulated for intramuscular injection.

7. The method for promoting muscle regeneration, tendon regeneration, or arteriogenesis according to claim 1, wherein at least 4 consecutive residues of the synthetic peptide are identical to residues 11-14 of SEQ ID NO: 1.

8. The method for promoting muscle regeneration, tendon regeneration, or arteriogenesis according to claim 7, wherein the synthetic peptide is formulated into a pharmaceutical composition comprising the synthetic peptide and a pharmaceutically acceptable carrier.

9. The method for promoting muscle regeneration, tendon regeneration, or arteriogenesis according to claim 8, wherein the pharmaceutically acceptable carrier is a polymeric material selected from the group consisting of alginate, gelatin, collagen, and poly(lactide-co-glycolide).

10. The method for promoting muscle regeneration, tendon regeneration, or arteriogenesis according to claim 9, wherein the pharmaceutically acceptable carrier is an alginate.

11. The method for promoting muscle regeneration, tendon regeneration, or arteriogenesis according to claim 10, wherein the pharmaceutical composition is formulated in a sustained-release form.

12. The method for promoting muscle regeneration, tendon regeneration, or arteriogenesis according to claim 1, wherein the synthetic peptide has the amino acid sequence of SEQ ID NO: 1, SEQ ID NO: 2, SEQ ID NO: 3, SEQ ID NO: 5, SEQ ID NO: 6, SEQ ID NO: 8, or SEQ ID NO: 9.

13. The method for promoting muscle regeneration, tendon regeneration, or arteriogenesis according to claim 12, wherein the synthetic peptide is formulated into a pharmaceutical composition comprising the synthetic peptide and a pharmaceutically acceptable carrier.

14. The method for promoting muscle regeneration, tendon regeneration, or arteriogenesis according to claim 13, wherein the pharmaceutically acceptable carrier is a polymeric material selected from the group consisting of alginate, gelatin, collagen, and poly(lactide-co-glycolide).

15. The method for promoting muscle regeneration, tendon regeneration, or arteriogenesis according to claim 14, wherein the pharmaceutically acceptable carrier is an alginate.

16. The method for promoting muscle regeneration, tendon regeneration, or arteriogenesis according to claim 15, wherein the pharmaceutical composition is formulated in a sustained-release form.

17. The method for promoting muscle regeneration, tendon regeneration, or arteriogenesis according to claim 1, wherein the synthetic peptide has the amino acid sequence of SEQ ID NO: 3, SEQ ID NO: 5, or SEQ ID NO: 6.

18. The method for promoting muscle regeneration, tendon regeneration, or arteriogenesis according to claim 17, wherein the synthetic peptide is formulated into a pharmaceutical composition comprising the synthetic peptide and a pharmaceutically acceptable carrier.

19. The method for promoting muscle regeneration, tendon regeneration, or arteriogenesis according to claim 18, wherein the pharmaceutically acceptable carrier is a polymeric material selected from the group consisting of alginate, gelatin, collagen, and poly(lactide-co-glycolide).

20. The method for promoting muscle regeneration, tendon regeneration, or arteriogenesis according to claim 19, wherein the pharmaceutically acceptable carrier is an alginate.

* * * * *

SEQUENCE LISTING

```
<160> NUMBER OF SEQ ID NOS: 14

<210> SEQ ID NO 1
<211> LENGTH: 39
<212> TYPE: PRT
<213> ORGANISM: Artificial Sequence
<220> FEATURE:
<223> OTHER INFORMATION: synthetic peptide

<400> SEQUENCE: 1

Leu Ser Val Ala Thr Ala Leu Ser Ala Leu Ser Leu Gly Ala Glu Gln
1               5                   10                  15

Arg Thr Glu Ser Ile Ile His Arg Ala Leu Tyr Tyr Asp Leu Ile Ser
            20                  25                  30

Ser Pro Asp Ile His Gly Thr
        35

<210> SEQ ID NO 2
<211> LENGTH: 34
<212> TYPE: PRT
<213> ORGANISM: Artificial Sequence
<220> FEATURE:
<223> OTHER INFORMATION: synthetic peptide

<400> SEQUENCE: 2
```

```
Ala Leu Ser Ala Leu Ser Leu Gly Ala Glu Gln Arg Thr Glu Ser Ile
1               5                   10                  15

Ile His Arg Ala Leu Tyr Tyr Asp Leu Ile Ser Ser Pro Asp Ile His
            20                  25                  30

Gly Thr

<210> SEQ ID NO 3
<211> LENGTH: 29
<212> TYPE: PRT
<213> ORGANISM: Artificial Sequence
<220> FEATURE:
<223> OTHER INFORMATION: synthetic peptide

<400> SEQUENCE: 3

Ser Leu Gly Ala Glu Gln Arg Thr Glu Ser Ile Ile His Arg Ala Leu
1               5                   10                  15

Tyr Tyr Asp Leu Ile Ser Ser Pro Asp Ile His Gly Thr
            20                  25

<210> SEQ ID NO 4
<211> LENGTH: 25
<212> TYPE: PRT
<213> ORGANISM: Artificial Sequence
<220> FEATURE:
<223> OTHER INFORMATION: synthetic peptide

<400> SEQUENCE: 4

Glu Gln Arg Thr Glu Ser Ile Ile His Arg Ala Leu Tyr Tyr Asp Leu
1               5                   10                  15

Ile Ser Ser Pro Asp Ile His Gly Thr
            20                  25

<210> SEQ ID NO 5
<211> LENGTH: 24
<212> TYPE: PRT
<213> ORGANISM: Artificial Sequence
<220> FEATURE:
<223> OTHER INFORMATION: synthetic peptide

<400> SEQUENCE: 5

Ser Leu Gly Ala Glu Gln Arg Thr Glu Ser Ile Ile His Arg Ala Leu
1               5                   10                  15

Tyr Tyr Asp Leu Ile Ser Ser Pro
            20

<210> SEQ ID NO 6
<211> LENGTH: 20
<212> TYPE: PRT
<213> ORGANISM: Artificial Sequence
<220> FEATURE:
<223> OTHER INFORMATION: synthetic peptide

<400> SEQUENCE: 6

Ser Leu Gly Ala Glu Gln Arg Thr Glu Ser Ile Ile His Arg Ala Leu
1               5                   10                  15

Tyr Tyr Asp Leu
            20

<210> SEQ ID NO 7
<211> LENGTH: 18
<212> TYPE: PRT
<213> ORGANISM: Artificial Sequence
<220> FEATURE:
```

<223> OTHER INFORMATION: synthetic peptide

<400> SEQUENCE: 7

Glu Gln Arg Thr Glu Ser Ile Ile His Arg Ala Leu Tyr Tyr Asp Leu
1               5                   10                  15

Ile Ser

<210> SEQ ID NO 8
<211> LENGTH: 29
<212> TYPE: PRT
<213> ORGANISM: Artificial Sequence
<220> FEATURE:
<223> OTHER INFORMATION: synthetic peptide

<400> SEQUENCE: 8

Ser Leu Gly Ala Glu His Arg Thr Glu Ser Val Ile His Arg Ala Leu
1               5                   10                  15

Tyr Tyr Asp Leu Ile Thr Asn Pro Asp Ile His Ser Thr
            20                  25

<210> SEQ ID NO 9
<211> LENGTH: 20
<212> TYPE: PRT
<213> ORGANISM: Artificial Sequence
<220> FEATURE:
<223> OTHER INFORMATION: synthetic peptide

<400> SEQUENCE: 9

Ser Leu Gly Ala Glu His Arg Thr Glu Ser Val Ile His Arg Ala Leu
1               5                   10                  15

Tyr Tyr Asp Leu
            20

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
agaatgagca atgggtggtc                                           20

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
ctcgacctcc ttggtagcag                                           20

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
agacagccgc atcttcttgt                                           20

<210> SEQ ID NO 13

```
<211> LENGTH: 20
<212> TYPE: DNA
<213> ORGANISM: Artificial Sequence
<220> FEATURE:
<223> OTHER INFORMATION: Primer

<400> SEQUENCE: 13
cttgccgtgg gtagagtcat                                            20

<210> SEQ ID NO 14
<211> LENGTH: 418
<212> TYPE: PRT
<213> ORGANISM: Homo sapiens

<400> SEQUENCE: 14
```

| | | | | | | | | | | | | | | | |
|---|---|---|---|---|---|---|---|---|---|---|---|---|---|---|---|
| Met | Gln | Ala | Leu | Val | Leu | Leu | Leu | Cys | Ile | Gly | Ala | Leu | Leu | Gly | His |
| 1 | | | | 5 | | | | | 10 | | | | | 15 | |
| Ser | Ser | Cys | Gln | Asn | Pro | Ala | Ser | Pro | Pro | Glu | Glu | Gly | Ser | Pro | Asp |
| | | | 20 | | | | | 25 | | | | | 30 | | |
| Pro | Asp | Ser | Thr | Gly | Ala | Leu | Val | Glu | Glu | Asp | Pro | Phe | Phe | Lys | |
| | | 35 | | | | | 40 | | | | | 45 | | | |
| Val | Pro | Val | Asn | Lys | Leu | Ala | Ala | Val | Ser | Asn | Phe | Gly | Tyr | Asp | |
| 50 | | | | | 55 | | | | | 60 | | | | | |
| Leu | Tyr | Arg | Val | Arg | Ser | Ser | Thr | Ser | Pro | Thr | Thr | Asn | Val | Leu | Leu |
| 65 | | | | | 70 | | | | | 75 | | | | | 80 |
| Ser | Pro | Leu | Ser | Val | Ala | Thr | Ala | Leu | Ser | Ala | Leu | Ser | Leu | Gly | Ala |
| | | | | 85 | | | | | 90 | | | | | 95 | |
| Glu | Gln | Arg | Thr | Glu | Ser | Ile | Ile | His | Arg | Ala | Leu | Tyr | Tyr | Asp | Leu |
| | | | 100 | | | | | 105 | | | | | 110 | | |
| Ile | Ser | Ser | Pro | Asp | Ile | His | Gly | Thr | Tyr | Lys | Glu | Leu | Leu | Asp | Thr |
| | | 115 | | | | | 120 | | | | | 125 | | | |
| Val | Thr | Ala | Pro | Gln | Lys | Asn | Leu | Lys | Ser | Ala | Ser | Arg | Ile | Val | Phe |
| 130 | | | | | 135 | | | | | 140 | | | | | |
| Glu | Lys | Lys | Leu | Arg | Ile | Lys | Ser | Ser | Phe | Val | Ala | Pro | Leu | Glu | Lys |
| 145 | | | | | 150 | | | | | 155 | | | | | 160 |
| Ser | Tyr | Gly | Thr | Arg | Pro | Arg | Val | Leu | Thr | Gly | Asn | Pro | Arg | Leu | Asp |
| | | | | 165 | | | | | 170 | | | | | 175 | |
| Leu | Gln | Glu | Ile | Asn | Asn | Trp | Val | Gln | Ala | Gln | Met | Lys | Gly | Lys | Leu |
| | | | 180 | | | | | 185 | | | | | 190 | | |
| Ala | Arg | Ser | Thr | Lys | Glu | Ile | Pro | Asp | Glu | Ile | Ser | Ile | Leu | Leu | Leu |
| | | 195 | | | | | 200 | | | | | 205 | | | |
| Gly | Val | Ala | His | Phe | Lys | Gly | Gln | Trp | Val | Thr | Lys | Phe | Asp | Ser | Arg |
| | 210 | | | | | 215 | | | | | 220 | | | | |
| Lys | Thr | Ser | Leu | Glu | Asp | Phe | Tyr | Leu | Asp | Glu | Glu | Arg | Thr | Val | Arg |
| 225 | | | | | 230 | | | | | 235 | | | | | 240 |
| Val | Pro | Met | Met | Ser | Asp | Pro | Lys | Ala | Val | Leu | Arg | Tyr | Gly | Leu | Asp |
| | | | | 245 | | | | | 250 | | | | | 255 | |
| Ser | Asp | Leu | Ser | Cys | Lys | Ile | Ala | Gln | Leu | Pro | Leu | Thr | Gly | Ser | Met |
| | | | 260 | | | | | 265 | | | | | 270 | | |
| Ser | Ile | Ile | Phe | Phe | Leu | Pro | Leu | Lys | Val | Thr | Gln | Asn | Leu | Thr | Leu |
| | | | 275 | | | | | 280 | | | | | 285 | | |
| Ile | Glu | Glu | Ser | Leu | Thr | Ser | Glu | Phe | Ile | His | Asp | Ile | Asp | Arg | Glu |
| | | | 290 | | | | | 295 | | | | | 300 | | |
| Leu | Lys | Thr | Val | Gln | Ala | Val | Leu | Thr | Val | Pro | Lys | Leu | Lys | Leu | Ser |
| 305 | | | | | 310 | | | | | 315 | | | | | 320 |
| Tyr | Glu | Gly | Glu | Val | Thr | Lys | Ser | Leu | Gln | Glu | Met | Lys | Leu | Gln | Ser |

-continued

```
                325                 330                 335
Leu Phe Asp Ser Pro Asp Phe Ser Lys Ile Thr Gly Lys Pro Ile Lys
            340                 345                 350

Leu Thr Gln Val Glu His Arg Ala Gly Phe Glu Trp Asn Glu Asp Gly
        355                 360                 365

Ala Gly Thr Thr Pro Ser Pro Gly Leu Gln Pro Ala His Leu Thr Phe
    370                 375                 380

Pro Leu Asp Tyr His Leu Asn Gln Pro Phe Ile Phe Val Leu Arg Asp
385                 390                 395                 400

Thr Asp Thr Gly Ala Leu Leu Phe Ile Gly Lys Ile Leu Asp Pro Arg
                405                 410                 415

Gly Pro
```